United States Patent
Yokoyama et al.

(10) Patent No.: US 9,525,140 B2
(45) Date of Patent: *Dec. 20, 2016

(54) ARYLAMINE COMPOUND USEFUL IN AN ORGANIC ELECTROLUMINESCENT DEVICE

(71) Applicant: HODOGAYA CHEMICAL CO., LTD., Tokyo (JP)

(72) Inventors: Norimasa Yokoyama, Ibaraki (JP); Shigeru Kusano, Ibaraki (JP); Shuichi Hayashi, Ibaraki (JP)

(73) Assignee: HODOGAYA CHEMICAL CO., LTD., Tokyo (JP)

(*) Notice: Subject to any disclaimer, the term of this patent is extended or adjusted under 35 U.S.C. 154(b) by 58 days.

This patent is subject to a terminal disclaimer.

(21) Appl. No.: 14/044,335

(22) Filed: Oct. 2, 2013

(65) Prior Publication Data
US 2014/0039221 A1 Feb. 6, 2014

Related U.S. Application Data

(63) Continuation of application No. 12/993,051, filed as application No. PCT/JP2009/059093 on May 15, 2009, now Pat. No. 8,771,841.

(30) Foreign Application Priority Data

May 16, 2008 (JP) ................................. 2008-129340
Jul. 2, 2008 (JP) ................................. 2008-173023

(51) Int. Cl.
*H01L 51/50* (2006.01)
*H01L 51/00* (2006.01)
(Continued)

(52) U.S. Cl.
CPC .......... *H01L 51/006* (2013.01); *C07D 471/04* (2013.01); *C09K 11/06* (2013.01); *H01L 51/0059* (2013.01);
(Continued)

(58) Field of Classification Search
None
See application file for complete search history.

(56) References Cited

U.S. PATENT DOCUMENTS 4,720,432 A 1/1988 VanSlyke et al.
4,885,211 A 12/1989 Tang et al.
(Continued)

FOREIGN PATENT DOCUMENTS

EP 1 582 516 A1 10/2005
JP 60-254045 12/1985
(Continued)

OTHER PUBLICATIONS

International Search Report issued Jun. 30, 2009 in PCT/JP09/59093 filed May 15, 2009.
(Continued)

*Primary Examiner* — Gregory Clark
(74) *Attorney, Agent, or Firm* — Oblon, McClelland, Maier & Neustadt, L.L.P.

(57) ABSTRACT

A problem of the invention is to provide an organic EL device having a high efficiency, a low driving voltage and a long life, by combining various materials for organic EL device, which are excellent in an injection or transportation performance of holes or electrons, and in stability and durability in a thin film, so as to enable the respective materials to effectively reveal their characteristics. The invention relates to an organic electroluminescent device including at least an anode electrode, a hole-injecting layer, a hole-transporting layer, an emitting layer, an electron-transporting layer and a cathode electrode in this order, in which the hole-injecting layer contains an arylamine compound having, in its molecule, a structure in which three or more triphenylamine structures are connected through a single bond or a hetero atom-free divalent group; and the hole-transporting layer contains an arylamine compound having two triphenylamine structures in its molecule.

8 Claims, 1 Drawing Sheet

(51) Int. Cl.
*C07D 471/04* (2006.01)
*C09K 11/06* (2006.01)

(52) U.S. Cl.
CPC .... *C09K 2211/1014* (2013.01); *H01L 51/0052* (2013.01); *H01L 51/0067* (2013.01); *H01L 51/0072* (2013.01); *H01L 51/5048* (2013.01)

(56) References Cited

U.S. PATENT DOCUMENTS

| | | | |
|---|---|---|---|
| 5,126,214 A | 6/1992 | Tokailin et al. | |
| 5,639,914 A | 6/1997 | Tomiyama et al. | |
| 5,707,747 A | 1/1998 | Tomiyama et al. | |
| 5,792,557 A | 8/1998 | Nakaya et al. | |
| 2002/0102434 A1 | 8/2002 | Inoue et al. | |
| 2002/0182439 A1 | 12/2002 | Tao et al. | |
| 2004/0253389 A1* | 12/2004 | Suzuki et al. | 428/1.1 |
| 2006/0028129 A1 | 2/2006 | Sakakibara et al. | |
| 2006/0068221 A1 | 3/2006 | Saitoh et al. | |
| 2006/0154105 A1 | 7/2006 | Yamamoto et al. | |
| 2006/0232198 A1* | 10/2006 | Kawamura | C07C 211/54 313/504 |
| 2006/0251918 A1 | 11/2006 | Iwakuma et al. | |
| 2007/0075635 A1 | 4/2007 | Yabunouchi et al. | |
| 2007/0285004 A1 | 12/2007 | Miki et al. | |
| 2008/0014464 A1 | 1/2008 | Kawamura et al. | |
| 2010/0012926 A1 | 1/2010 | Lee et al. | |
| 2010/0230660 A1 | 9/2010 | Yokoyama et al. | |

FOREIGN PATENT DOCUMENTS

| | | | |
|---|---|---|---|
| JP | 61-129648 | 6/1986 | |
| JP | 2-15595 | 1/1990 | |
| JP | 3-152897 | 6/1991 | |
| JP | 4-161480 | 6/1992 | |
| JP | 6 314594 | 11/1994 | |
| JP | 7 126226 | 5/1995 | |
| JP | 7-126615 A | 5/1995 | |
| JP | 8 48656 | 2/1996 | |
| JP | 8 291115 | 11/1996 | |
| JP | 10-088119 A | 4/1998 | |
| JP | 3194657 | 6/2001 | |
| JP | 2002-179630 A | 6/2002 | |
| JP | 2003-146950 | 5/2003 | |
| JP | 2004-87363 | 3/2004 | |
| JP | 3529735 | 3/2004 | |
| JP | 2004-186027 A | 7/2004 | |
| JP | 2005-85599 A | 3/2005 | |
| JP | 2005-108804 A | 4/2005 | |
| JP | 2005-216683 A | 8/2005 | |
| JP | 2005-285471 A | 10/2005 | |
| JP | 2006-5355 A | 1/2006 | |
| JP | 2006-73636 A | 3/2006 | |
| JP | 2006-278004 A | 10/2006 | |
| JP | 2007 84439 | 4/2007 | |
| JP | 2007-269738 A | 10/2007 | |
| JP | 2008-007424 A | 1/2008 | |
| WO | 2004 053019 | 6/2004 | |
| WO | WO2006/120859 A1 * | 11/2006 | H01L 51/50 |
| WO | 2008 020611 | 2/2008 | |

OTHER PUBLICATIONS

Wakimoto, Takeo: "Optimization of driving lifetime durability in organic LED devices using phosphorescent guest emitter", Japan Applied Physics Ninth Workshop Preprint, pp. 23-31, (2001).

Hosokawa C. et al., Japan Society of Applied Physics Ninth Workshop Preprint, pp. 55-61, (2001).

Extended Search Report issued Apr. 6, 2011 in European Application No. 09746681.7.

Extended European Search Report issued Feb. 27, 2014 in Patent Application No. 13004407.6.

Office Action issued Dec. 10, 2013 in Japanese Patent Application No. 2010-512037 (with English language translation).

Office Action and Search Report issued on Nov. 7, 2014 in the corresponding Taiwanese Patent Application No. 102131231 (with English Translation).

Office Action issued on Nov. 18, 2014 in the corresponding Japanese Patent Application No. 2014-018741 (with English Translation).

Zhong Hui Li et al.; "Synthesis and Functional Properties of Strongly Luminescent Diphenylamino End-Capped Oligophenylenes"; The Journal of Organic Chemistry; Jun. 6, 2004; vol. 69; Issue 3; pp. 921-927.

Office Action issued Jun. 30, 2016 in Chinese Patent Application No. 201510020875.2 (with English translation).

Jhun Mo Son et al.; "Condensation polymerization of Triphenylamine with carbonyl compounds"; Macromol. Chemi. Phys., Jan. 31, 1999, vol. 200, pp. 65-70.

* cited by examiner

ARYLAMINE COMPOUND USEFUL IN AN ORGANIC ELECTROLUMINESCENT DEVICE

CROSS REFERENCE TO RELATED APPLICATIONS

The present application is a Continuation of U.S. application Ser. No. 12/993,051, filed Nov. 16, 2010, pending, which is a 371 national stage application from PCT/JP2009/059093, filed May 15, 2009, and claims priority to Japanese Patent Application No. 2008-129340 filed on May 16, 2008 and Japanese Patent Application No. 2008-173023 filed on Jul. 2, 2008, the contents of each of which are hereby incorporated by reference.

TECHNICAL FIELD

The present invention relates to an organic electroluminescent device which is a self-luminescent device suitable for various display devices. More specifically, the invention relates to an organic electroluminescent device (hereinafter referred to as "organic EL device") using plural kinds of specified arylamine derivatives (and specified pyridine derivatives).

BACKGROUND ART

Since organic EL devices are self-luminescent devices, they are bright and excellent in visibility as compared with liquid-crystalline devices and capable of giving clear display. Therefore, the organic EL devices have been actively studied.

In 1987, C. W. Tang et al. of Eastman Kodak Company put an organic EL device using organic materials into practical use by developing a device having a multilayered structure wherein various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1000 cd/m$^2$ or more at a voltage of 10 V or lower (see e.g., Patent Documents 1 and 2).
Patent Document 1: JP-A-8-48656
Patent Document 2: Japanese Patent No. 3194657

To date, many improvements have been performed for practical utilization of the organic EL devices, and high efficiency and durability have been achieved by an electroluminescent device wherein an anode, a hole-injecting layer, a hole-transporting layer, an emitting layer, an electron-transporting layer, an electron-injecting layer, and a cathode are sequentially provided on a substrate, to further segmentalize various roles of the multilayered structure (see e.g., Non-Patent Document 1).
Non-Patent Document 1: Japan Society of Applied Physics Ninth Workshop Preprint, pp. 55-61 (2001)

Moreover, for the purpose of further improvement of luminous efficiency, utilization of triplet exciton has been attempted and utilization of a phosphorescent material has been investigated (see e.g., Non-Patent Document 2).
Non-Patent Document 2: Japan Society of Applied Physics Ninth Workshop Preprint, pp. 23-31 (2001)

The emitting layer can be also prepared by doping a charge-transporting compound, generally called a host material, with a fluorescent material or a phosphorescent material. As described in the above-mentioned Non-Patent Document, the choice of the organic materials in organic EL devices remarkably affects various properties such as efficiency and durability of the devices (see Non-Patent Document 2).

In the organic EL devices, the charges injected from the both electrodes are recombined in the emitting layer to attain light emission. In order to obtain an organic EL device having a high efficiency, a low driving voltage and a long life, it is necessary to provide a device with an excellent carrier balance, in which electrons or holes can be efficiently injected and transported and the both can be efficiently recombined.

As a hole-injecting material which is used for the organic EL devices, phthalocyanines such as copper phthalocyanine (hereinafter referred to as "CuPc") were proposed at the beginning (see, e.g., Patent Document 3). However, since the phthalocyanines have absorption in the visible range, materials having a phenylenediamine structure have become widely used (see, e.g., Patent Document 4). On the other hand, as a hole-transporting material, arylamine based materials containing a benzidine skeleton have been used (see, e.g., Patent Document 5).
Patent Document 3: U.S. Pat. No. 4,720,432
Patent Document 4: JP-A-8-291115
Patent Document 5: Japanese Patent No. 3529735

A representative light-emitting material, tris(8-hydroxyquinoline)aluminum (hereinafter referred to as "Alq$_3$") is commonly used as an electron-transporting material. However, as compared with a hole mobility which generally used hole-transporting materials have, an electron mobility which Alq$_3$ has is low, and Alq$_3$ has a work function of 5.8 eV so that it cannot be considered that Alq$_3$ has sufficient hole-blocking ability. Therefore, a part of the holes passes through the emitting layer, resulting in lowering of the efficiency.

Furthermore, for the purpose of efficiently achieving hole injection or electron injection from an anode or a cathode into the emitting layer, there has been developed a device in which a value of ionization potential and a value of electron affinity which material has are set up in stages and two or more layers are laminated with respect to each of a hole-injecting layer and an electron-injecting layer (see, e.g., Patent Document 6). However, it cannot be said that the used materials are sufficient in all of luminous efficiency, driving voltage and device life.
Patent Document 6: JP-A-6-314594

In usual, since the hole-transporting layer is an extremely thin film, it is influenced by roughness of the surface of an ITO electrode, and there is a high probability of occurrence of defective products in the prepared device due to the occurrence of a short circuit or the like. When a film thickness of the hole-transporting layer is made thick, the roughness of the surface of the ITO electrode can be hidden, and it can reduce the probability of occurrence of defective products in the prepared device. However, when the film thickness of the hole-transporting layer is made thick, the driving voltage arises and exceeds a practical driving voltage.

For the purposes of improving device characteristics of organic EL devices and enhancing a yield of the device preparation, it has been demanded a device capable of achieving efficient recombination of holes and electrons and having a high luminous efficiency, a low driving voltage and a long life, by combining materials which are excellent in an injection or transportation performance of holes or electrons, and in stability and durability in a thin film.

Also, for the purpose of improving device characteristics of organic EL devices, it has been demanded a device with a good carrier balance and having a high efficiency, a low driving voltage and a long life, by combining materials which are excellent in an injection and transportation performance of holes or electrons, and in stability and durability in a thin film.

SUMMARY OF THE INVENTION

Problems to be Solved by the Invention

An object of the invention is to provide an organic EL device having a high efficiency, a low driving voltage and a long life, by combining various materials for organic EL device, which are excellent in an injection or transportation performance of holes or electrons, and in stability and durability in a thin film, so as to enable the respective materials to effectively reveal their characteristics. As physical characteristics of an organic compound which is suited in the invention, there may be mentioned (1) a good hole or electron injection characteristic, (2) a high hole or electron mobility, (3) an excellent electron- or hole-blocking ability, (4) good stability in a thin-film state and (5) excellent thermal resistance. Also, as physical characteristics of a device which is suited in the invention, there may be mentioned (1) a high luminous efficiency, (2) a low emission initiation voltage, (3) a low practical driving voltage and (4) a long life.

pyridine derivative and prepared various organic EL devices by combining the compounds so as to take a good carrier balance, with focusing on the fact that a pyridine derivative which exhibits affinity to electrons is excellent in an electron-injecting or transporting ability, and in stability and durability in a thin film, and they evaluated extensively and intensively the characteristics of the devices. As a result, they have accomplished the invention.

That is, the invention provides the following organic EL devices.

1) An organic electroluminescent device comprising at least an anode electrode, a hole-injecting layer, a hole-transporting layer, an emitting layer, an electron-transporting layer and a cathode electrode in this order, wherein the hole-injecting layer contains an arylamine compound having, in its molecule, a structure in which three or more triphenylamine structures are connected through a single bond or a hetero atom-free divalent group; and the hole-transporting layer contains an arylamine compound having two triphenylamine structures in its molecule.

2) The organic electroluminescent device according to the above 1), wherein the arylamine compound having, in its molecule, a structure in which three or more triphenylamine structures are connected through a single bond or a hetero atom-free divalent group is an arylamine compound represented by the following general formula (2):

[Chem. 1]

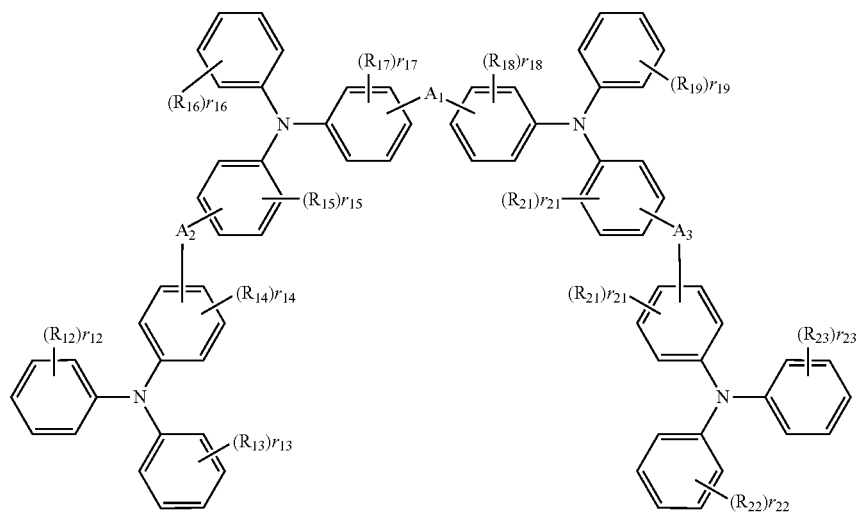

(2)

Means for Solving the Problems

Then, in order to attain the foregoing object, the present inventors chose specified two kinds of arylamine compounds and prepared various organic EL devices by combining the compounds such that holes can be efficiently injected and transported into an emitting layer, with focusing on the fact that an arylamine based material is excellent in a hole-injecting or transporting ability, and in stability and durability in a thin film, and they evaluated extensively and intensively the characteristics of the devices. Also, they chose a specified arylamine compound and a specified wherein $R_{12}$ to $R_{23}$ may be the same or different and each represents a hydrogen atom, a fluorine atom, a chlorine atom, a cyano group, a trifluoromethyl group, a linear or branched alkyl group having from 1 to 6 carbon atoms, a linear or branched alkenyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group, and when a plurality of these substituents are bonded on the same benzene ring, they may be bonded to each other to form a ring; $r_{12}$ to $r_{23}$ each represents an integer of from 1 to 4; and $A_1$, $A_2$ and $A_3$ may be the same or different and each represents a divalent group represented by one of the following structural formulae (B) to (F) or a single bond:

[Chem. 2]

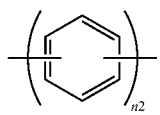
(B)

wherein n2 represents an integer of from 1 to 3.

[Chem. 3]

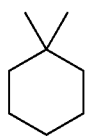
(C)

[Chem. 4]

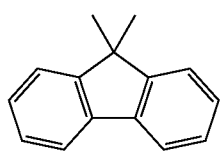
(D)

[Chem. 5]

—$CH_2$—
(E)

[Chem. 6]

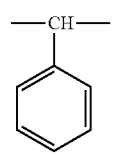
(F)

3) The organic electroluminescent device according to the above 1) or 2), wherein the arylamine compound having two triphenylamine structures in its molecule is an arylamine compound represented by the following general formula (3):

[Chem. 7]

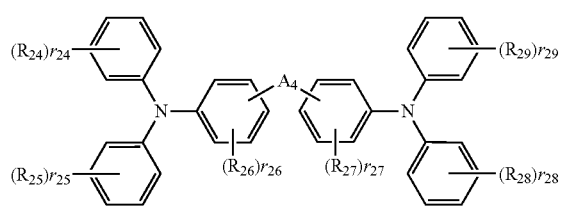
(3)

wherein $R_{24}$ to $R_{29}$ may be the same or different and each represents a hydrogen atom, a fluorine atom, a chlorine atom, a cyano group, a trifluoromethyl group, a linear or branched alkyl group having from 1 to 6 carbon atoms, a linear or branched alkenyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group, and when a plurality of these substituents are bonded on the same benzene ring, they may be bonded to each other to form a ring; $r_{24}$ to $r_{29}$ each represents an integer of from 1 to 4; and $A_4$ represents a divalent group represented by one of the following structural formulae (B) to (F) or a single bond:

[Chem. 8]

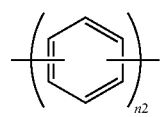
(B)

wherein n2 represents an integer of from 1 to 3.

[Chem. 9]

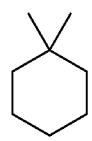
(C)

[Chem. 10]

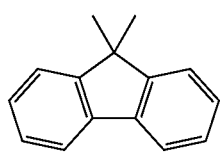
(D)

[Chem. 11]

—$CH_2$—
(E)

[Chem. 12]

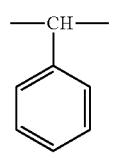
(F)

4) The organic electroluminescent device according to any one of the above 1) to 3), wherein the hole-transporting layer has a film thickness of from 20 to 300 nm.

5) The organic electroluminescent device according to the above 1), wherein the electron-transporting layer contains a compound having a pyridine ring and a pyridoindole ring in its molecule and represented by the following general formula (1):

[Chem. 13]

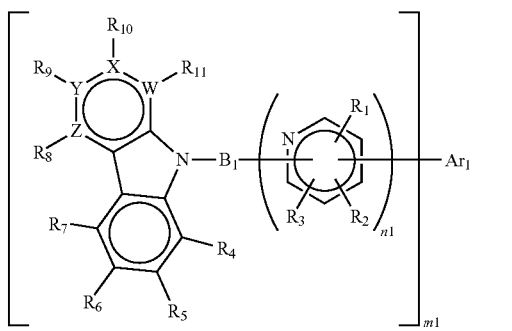

wherein $Ar_1$ represents a substituted or unsubstituted aromatic hydrocarbon group, a substituted or unsubstituted aromatic heterocyclic group or a substituted or unsubstituted condensed polycyclic aromatic group; $R_1$ to $R_{11}$ may be the same or different and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; B1 represents a substituted or unsubstituted aromatic hydrocarbon divalent group, a substituted or unsubstituted aromatic heterocyclic divalent group, a substituted or unsubstituted condensed polycyclic aromatic divalent group or a single bond; m1 and n1 each represents an integer of from 1 to 3; and W, X, Y and Z each represents a carbon atom or a nitrogen atom, provided that when m1 is 2, and when m1 is 3, then n1 is 1, and only one of W, X, Y and Z represents a nitrogen atom, and the nitrogen atom does not have the substituent of any of $R_8$ to $R_{11}$.

6) The organic electroluminescent device according to the above 5), wherein the arylamine compound having, in its molecule, a structure in which three or more triphenylamine structures are connected through a single bond or a hetero atom-free divalent group is an arylamine compound represented by the above general formula (2).

7) The organic electroluminescent device according to the above 5) or 6), wherein the arylamine compound having two triphenylamine structures in its molecule is an arylamine compound represented by the above general formula (3).

8) The organic electroluminescent device according to any one of the above 5) to 7), wherein the compound having a pyridine ring and a pyridoindole ring in its molecule is a compound represented by the following general formula (4):

[Chem. 14]

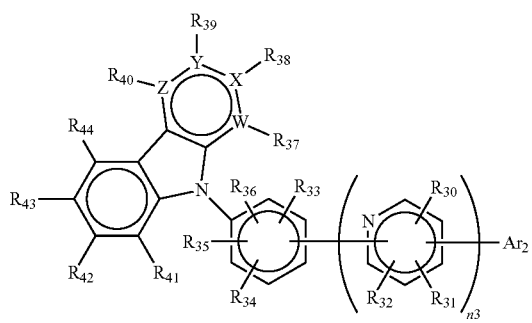

wherein $Ar_2$ represents a substituted or unsubstituted aromatic hydrocarbon group, a substituted or unsubstituted aromatic heterocyclic group or a substituted or unsubstituted condensed polycyclic aromatic group; $R_{30}$ to $R_{44}$ may be the same or different and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; n3 represents an integer of from 1 to 3; and W, X, Y and Z each represents a carbon atom or a nitrogen atom, provided that only one of W, X, Y and Z represents a nitrogen atom, and the nitrogen atom does not have the substituent of any of $R_{37}$ to $R_{40}$.

9) The organic electroluminescent device according to any one of the above 5) to 7), wherein the compound having a pyridine ring and a pyridoindole ring in its molecule is a compound represented by the following general formula (5):

[Chem. 15]

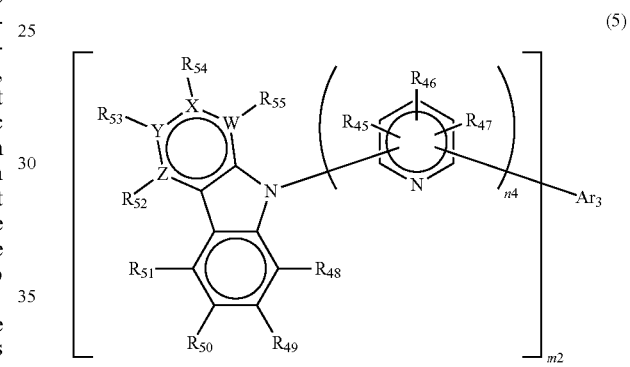

wherein $Ar_a$ represents a substituted or unsubstituted aromatic hydrocarbon group, a substituted or unsubstituted aromatic heterocyclic group or a substituted or unsubstituted condensed polycyclic aromatic group; $R_{45}$ to $R_{55}$ may be the same or different and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group or a substituted or unsubstituted condensed polycyclic aromatic group; m2 and n4 each represents an integer of from 1 to 3; and W, X, Y and Z each represents a carbon atom or a nitrogen atom, provided that when m2 is 2, and when m2 is 3, then n4 is 1, and only one of W, X, Y and Z represents a nitrogen atom, and the nitrogen atom does not have the substituent of any of $R_{52}$ to $R_{55}$.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $R_{12}$ to $R_{23}$ in the general formula (2), include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted condensed polycyclic aromatic group", represented by $R_{12}$ to $R_{23}$ in the general formula (2) include a fluorine atom, a chlorine atom, a trifluoromethyl group, a linear or branched alkyl group having 1 to 6 carbon atoms, a phenyl group, biphenylyl group, a terphenylyl group, a tetrakisphenyl group, a styryl group, a naphthyl group, a flluorenyl group, a phenanthryl group, indenyl group, and a pyrenyl group. These substituents may be further substituted.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $R_{24}$ to $R_{29}$ in the general formula (3), include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted condensed polycyclic aromatic group", represented by $R_{24}$ to $R_{29}$ in the general formula (3) include a fluorine atom, a chlorine atom, a trifluoromethyl group, a linear or branched alkyl group having 1 to 6 carbon atoms, a phenyl group, biphenylyl group, a terphenylyl group, a tetrakisphenyl group, a styryl group, a naphthyl group, a flluorenyl group, a phenanthryl group, indenyl group, and a pyrenyl group, and they may, be further substituted.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $Ar_1$ in the general formula (1), include the following compounds such as a phenyl group, a biphenyl group, a terphenylyl group, tetrakisphenyl group, a styryl group, a naphthyl group, an anthryl group, an acenaphtenyl group, a fluorenyl group, a phenanthryl group, an indenyl group, a pyrenyl group, a pyridyl group, a pyrimidyl group, a pyridoindolyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted condensed polycyclic aromatic group", represented by $Ar_1$ in the general formula (1) include a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group, and a benzothiazolyl group. These substituents may be further substituted.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $R_1$ to $R_{11}$ in the general formula (1), include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted condensed polycyclic aromatic group", represented by $R_1$ to $R_{11}$ in the general formula (1) include a fluorine atom, a chlorine atom, a trifluoromethyl group, a linear or branched alkyl group having 1 to 6 carbon atoms, a phenyl group, biphenylyl group, a terphenylyl group, a tetrakisphenyl group, a styryl group, a naphthyl group, a flluorenyl group, a phenanthryl group, indenyl group, and a pyrenyl group. These substituents may be further substituted.

Specific examples of the aromatic hydrocarbon divalent group, the aromatic heterocyclic divalent group or the condensed polycyclic aromatic divalent group in the "substituted or unsubstituted aromatic hydrocarbon divalent group", the "substituted or unsubstituted aromatic heterocyclic divalent group" or the "substituted or unsubstituted condensed polycyclic aromatic divalent group", which is presented by $B_1$ in the general formula (1), include a phenylene group, a biphenylylene group, a terphenylylene group, a tetrakisphenylene group, a naphthylene group, an anthrylene group, a fluorenylene group, a phenanthrolylene group, an indenylene group, a pyrenylene group, a pyridinylene group, a pyrimidinylene group, a quinolylene group, an isoquinolylene group, an indolylene group, a carbazolylene group, a quinoxalylene group, a benzoimidazolylene group, a pyrazolylene group, a naphthyridinylene group, a phenanthrolinylene group and an acridinylene group.

Specific examples of the substituent in the "substituted or unsubstituted aromatic hydrocarbon divalent group", the "substituted or unsubstituted aromatic heterocyclic divalent group" or the "substituted or unsubstituted condensed polycyclic aromatic divalent group", which is presented by $B_1$ in the general formula (1), include a fluorine atom, a chlorine atom, a trifluoromethyl group, a linear or branched alkyl group having 1 to 6 carbon atoms, a phenyl group, biphenylyl group, a terphenylyl group, a tetrakisphenyl group, a styryl group, a naphthyl group, a flluorenyl group, a phenanthryl group, indenyl group, and a pyrenyl group. These substituents may be further substituted.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $Ar_2$ in the general formula (4), include the following compounds such as a phenyl group, a biphenyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a pyridoindolyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted condensed polycyclic aromatic group", represented by $Ar_2$ in the general formula (4) include a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group, and a benzothiazolyl group. These substituents may be further substituted.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $R_{30}$ to $R_{44}$ in the general formula (4), include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted condensed polycyclic aromatic group", represented by $R_{30}$ to $R_{44}$ in the general formula (4) include a fluorine atom, a chlorine atom, a trifluoromethyl group, a linear or branched alkyl group having 1 to 6 carbon atoms, a phenyl group, biphenylyl group, a terphenylyl group, a tetrakisphenyl group, a styryl group, a naphthyl group, a flluorenyl group, a phenanthryl group, indenyl group, and a pyrenyl group. These substituents may be further substituted.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $Ar_3$ in the general formula (5), include the following compounds such as a phenyl group, a biphenyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a pyridoindolyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted or unsubstituted condensed polycyclic aromatic group", represented by $Ar_3$ in the general formula (5) include a fluorine atom, a chlorine atom, a cyano group, a hydroxyl group, a nitro group, an alkyl group, a cycloalkyl group, an alkoxy group, an amino group, a phenyl group, a naphthyl group, an anthryl group, a styryl group, a pyridyl group, a pyridoindolyl group, a quinolyl group, and a benzothiazolyl group. These substituents may be further substituted.

Specific examples of the aromatic hydrocarbon group, aromatic heterocyclic group, or condensed polycyclic aromatic group in the "substituted or unsubstituted aromatic hydrocarbon group", the "substituted or unsubstituted aromatic heterocyclic group", or the "substituted or unsubstituted condensed polycyclic aromatic group", which is represented by $R_{45}$ to $R_{55}$ in the general formula (5), include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothiophenyl group, a naphthyridinyl group, a phenanthrolinyl group, and an acridinyl group.

Specific examples of the substituent in the "substituted aromatic hydrocarbon group", the "substituted aromatic heterocyclic group", or the "substituted condensed polycyclic aromatic group", represented by $R_{45}$ to $R_{55}$ in the general formula (5) include a fluorine atom, a chlorine atom, a trifluoromethyl group, a linear or branched alkyl group having 1 to 6 carbon atoms, a phenyl group, biphenylyl group, a terphenylyl group, a tetrakisphenyl group, a styryl group, a naphthyl group, a flluorenyl group, a phenanthryl group, indenyl group, and a pyrenyl group. These substituents may be further substituted.

The arylamine compound having, in its molecule, a structure in which three or more triphenylamine structures are connected through a single bond or a hetero atom-free divalent group, as represented by the foregoing general formula (2), or the arylamine compound having two triphenylamine structures in its molecule, as represented by the foregoing general formula (3), both of which arylamine compounds are used for the organic EL device of the invention, can be used as a constituent material of a hole-injecting layer or a hole-transporting layer of the organic EL device.

The arylamine compound having, in its molecule, a structure in which three or more triphenylamine structures are connected through a single bond or a hetero atom-free divalent group, as represented by the foregoing general formula (2), has a high hole mobility as compared with the arylamine compound having two triphenylamine structures in its molecule, as represented by the foregoing general formula (3), and therefore is a preferred compound as a material of the hole-injection layer.

The compound having a pyridine ring and a pyridoindole ring in its molecule (specified pyridine derivative used in the invention), as represented by the foregoing general formula (1), the foregoing general formula (4) or the foregoing general formula (5), which is used for the organic EL device of the invention, can be used as a constituent material of the electron-transporting layer of the organic EL device.

In the organic EL device of the invention, materials for organic EL device which are excellent in an injection or transportation performance of holes or electrons, and in stability and durability in a thin film are combined while taking into consideration a carrier balance. Therefore, in comparison with conventional organic EL devices, an efficiency of hole injection into the hole-injecting layer is enhanced, and an efficiency of hole transport from the hole-transporting layer into the emitting layer is also enhanced (furthermore, in an embodiment using the specified pyridine derivative, an efficiency of electron transport from the electron-transporting layer to the emitting layer is also enhanced). Thus, not only the luminous efficiency can be enhanced, but also the driving voltage can be lowered, thereby enhancing the durability of the organic EL device.

It has become possible to realize an organic EL device having a high efficiency, a low driving voltage and a long life.

Advantageous Effects

In the organic EL device of the invention, by choosing a combination of specified two kinds of arylamine compounds which are excellent in an injection or transportation performance of holes or electrons, and in stability and durability in a thin film, and which are able to effectively reveal a role of injection or transportation of holes, it is possible to realize an organic EL device capable of efficiently injecting or transporting holes into an emitting layer and having a high efficiency, a low driving voltage and a long life. Also, by choosing a specified arylamine compound and a specified pyridine derivative and combining them so as to take a carrier balance, it is possible to realize an organic EL device having a high efficiency, a low driving voltage and a long life. According to the invention, the luminous efficiency, driving voltage and durability of conventional organic EL devices can be improved.

MODES FOR CARRYING OUT THE INVENTION

Figure 1:
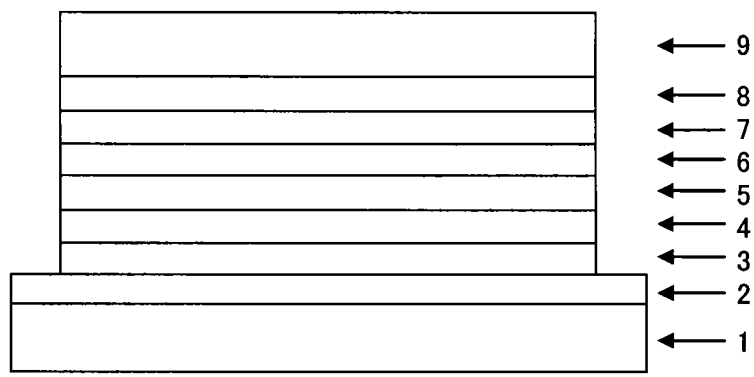
FIG. 1 is a view showing a configuration example of an EL device of the invention.

Specific examples of preferred compounds of the arylamine compound having, in its molecule, a structure in which three or more triphenylamine structures are connected through a single bond or a hetero atom-free divalent group, as represented by the foregoing general formula (2), which is suitably used for the organic EL device of the invention, are given below, but it should not be construed that the invention is limited to these compounds.

[Chem. 16]

(2-1)

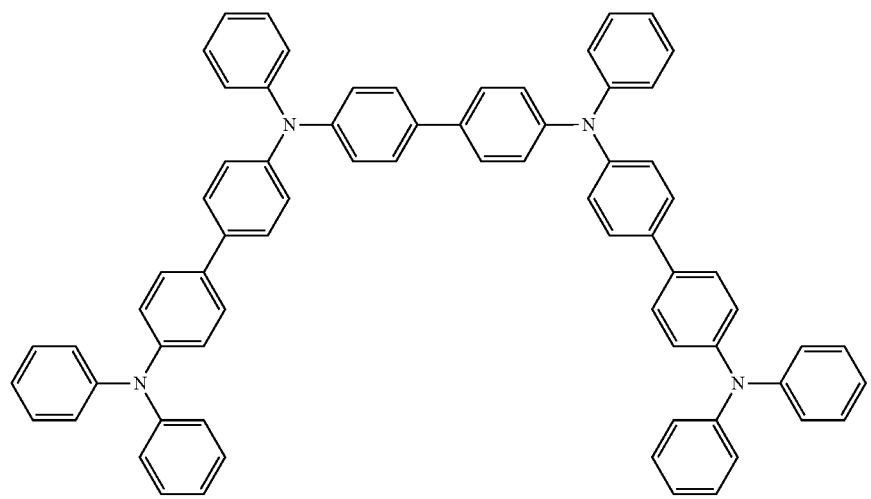

-continued
[Chem. 17]
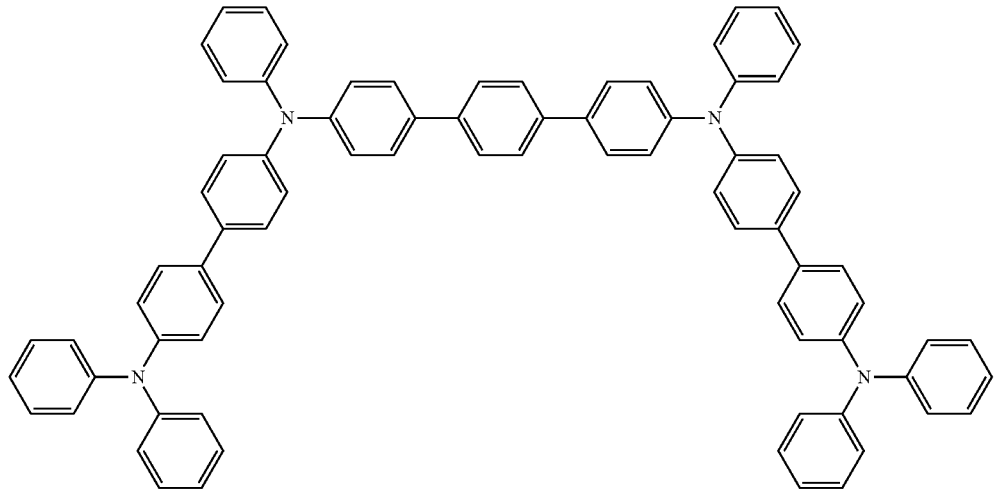
(2-2)
[Chem. 18]
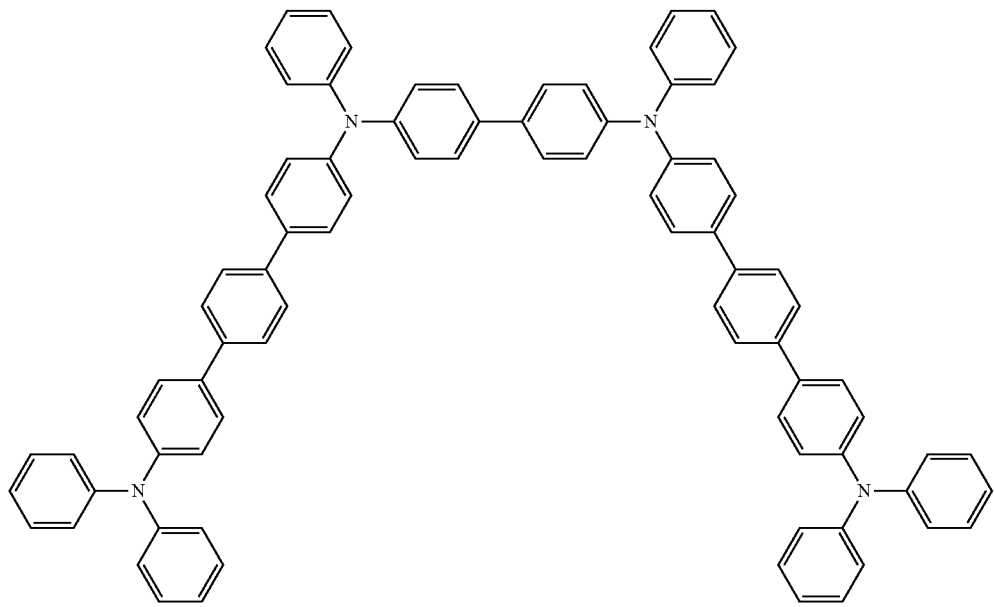
(2-3)

-continued
[Chem. 19]
(2-4)
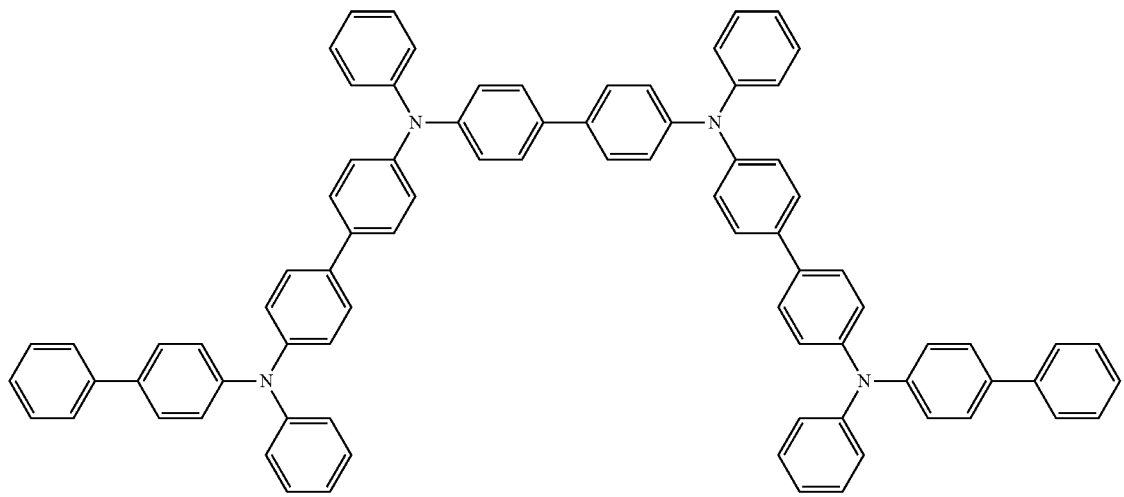
[Chem. 20]
(2-5)
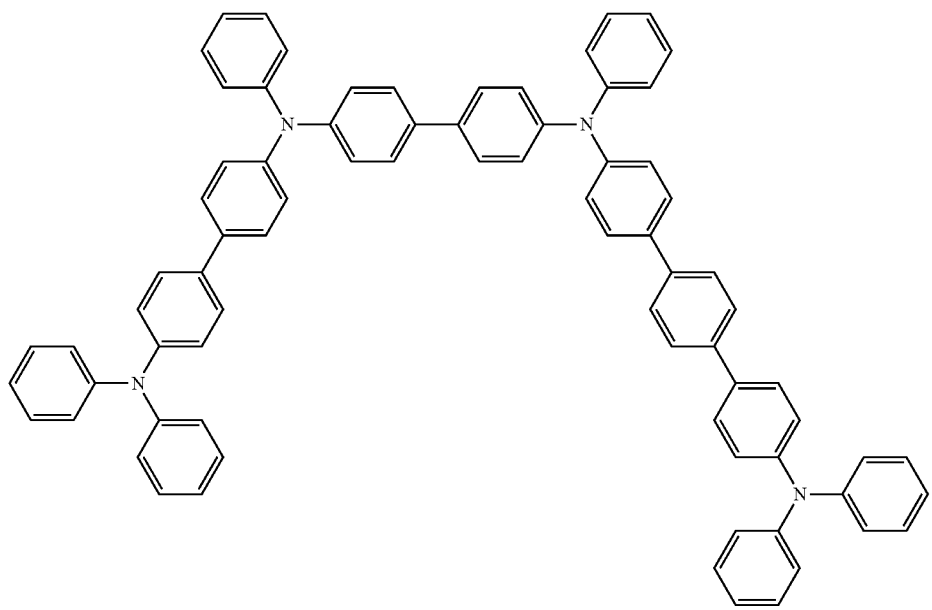
[Chem. 21]
(2-6)
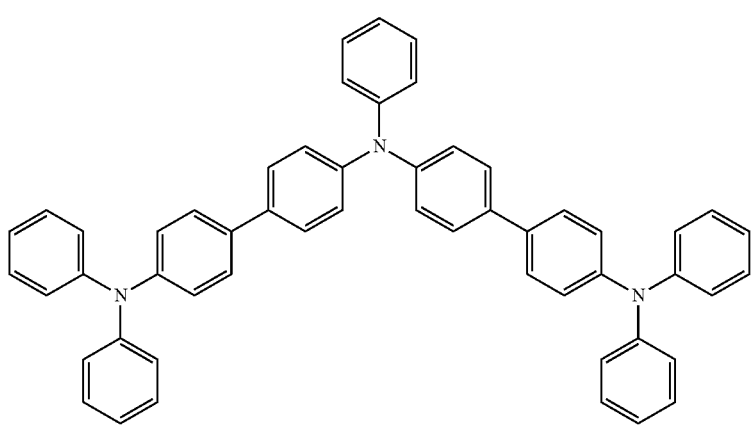

[Chem. 22]
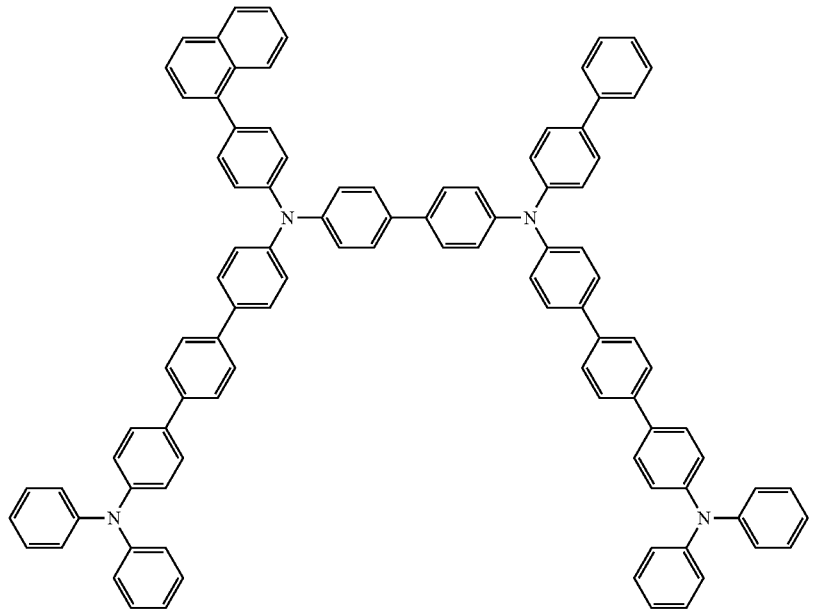
(2-7)
[Chem. 23]
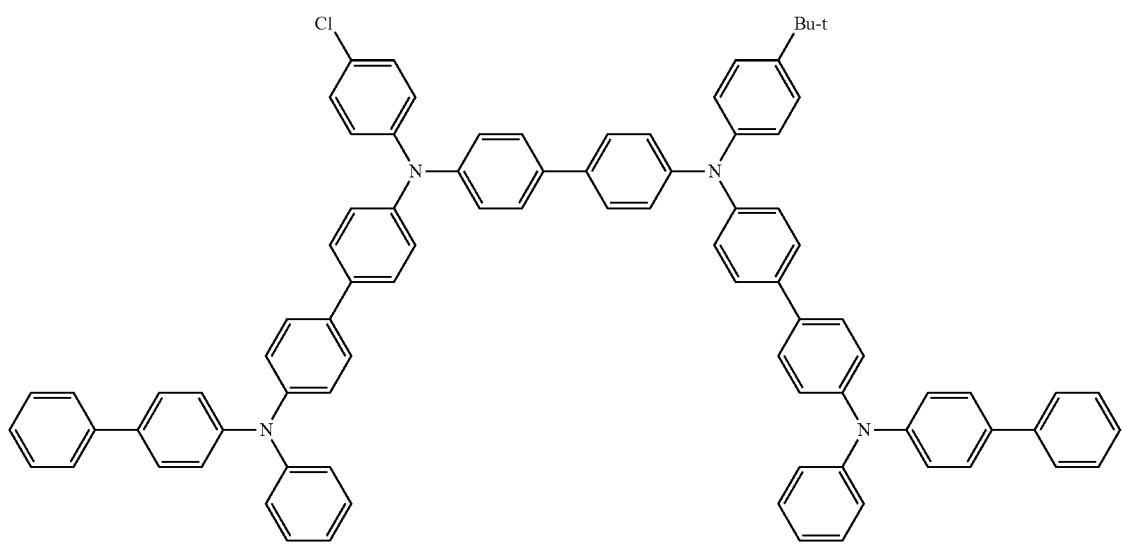
(2-8)

[Chem. 24]
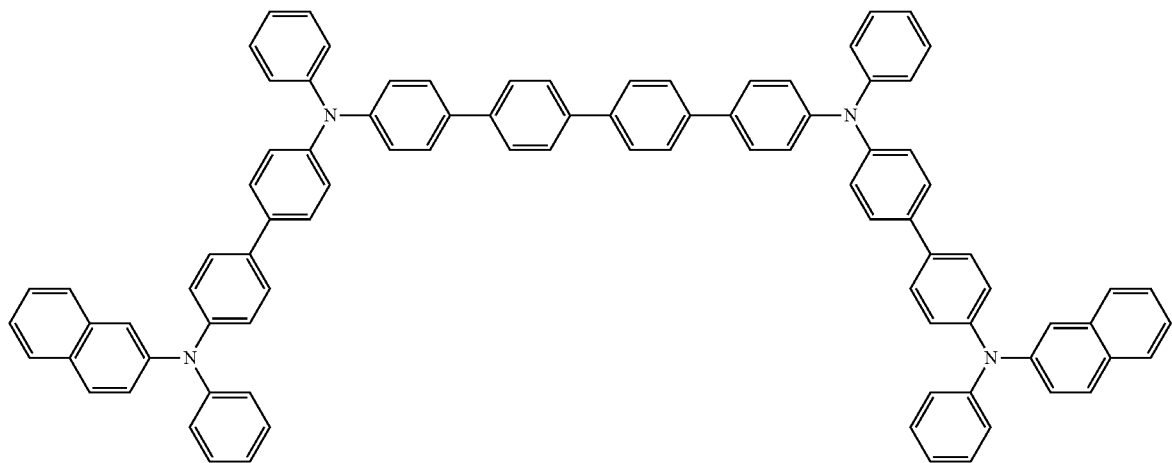
(2-9)
[Chem. 25]
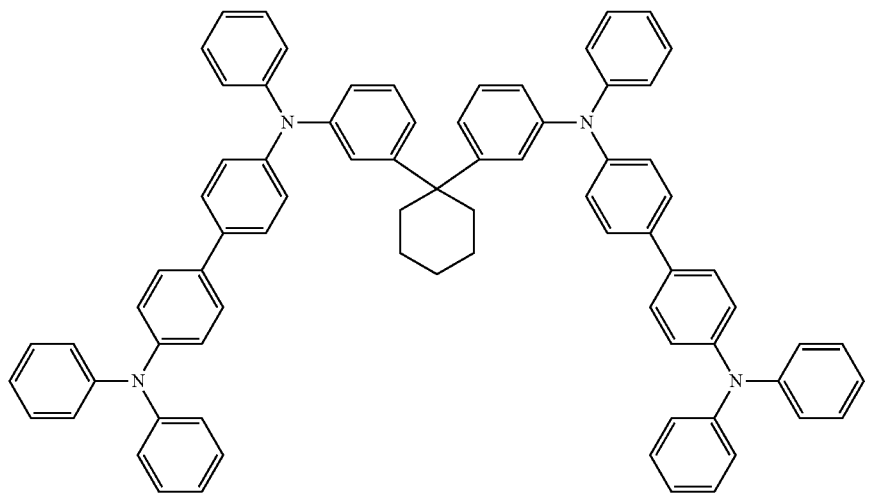
(2-10)
[Chem. 26]
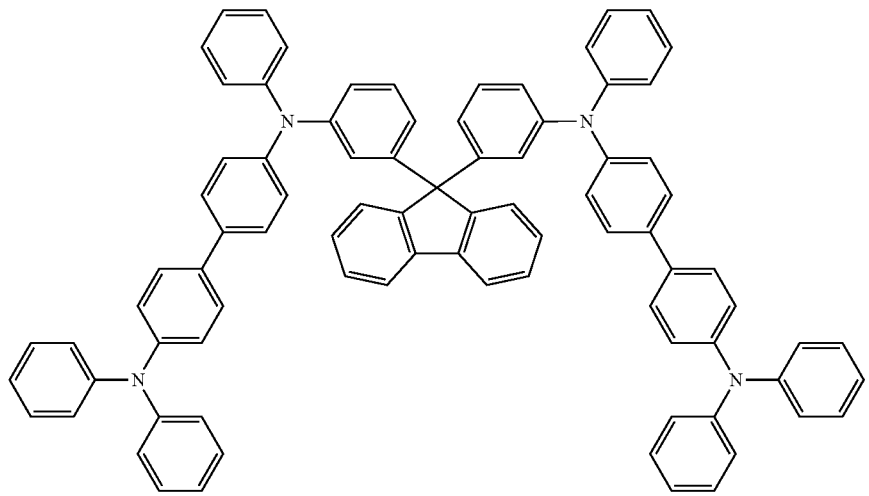
(2-11)

[Chem. 27]
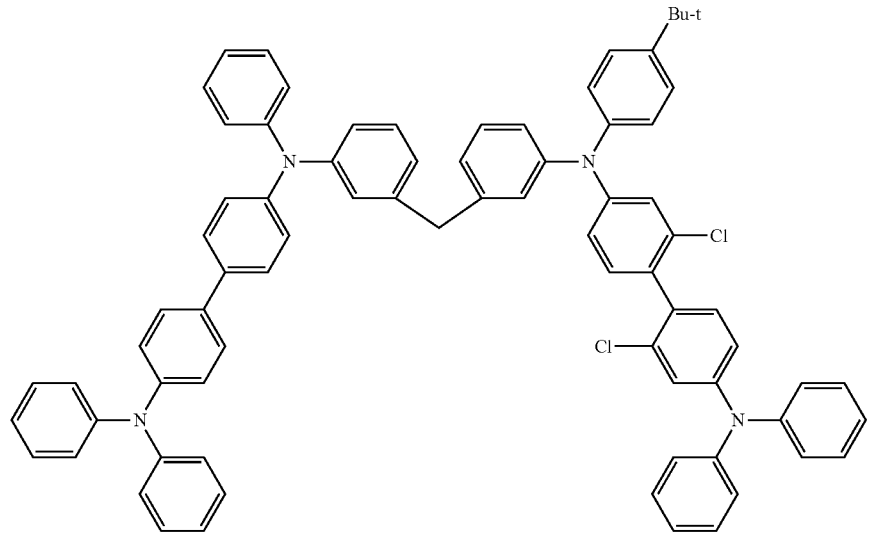
(2-12)
[Chem. 28]
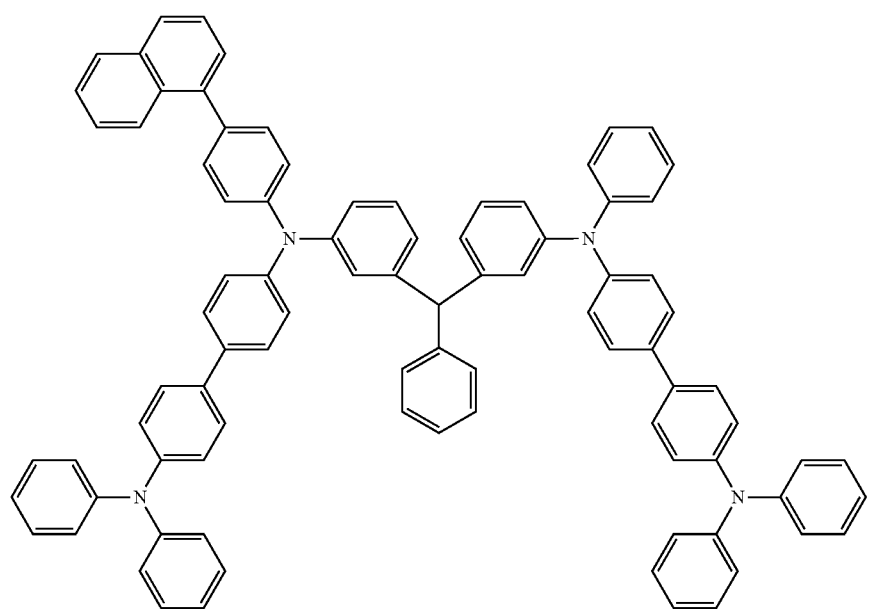
(2-13)

(2-14)
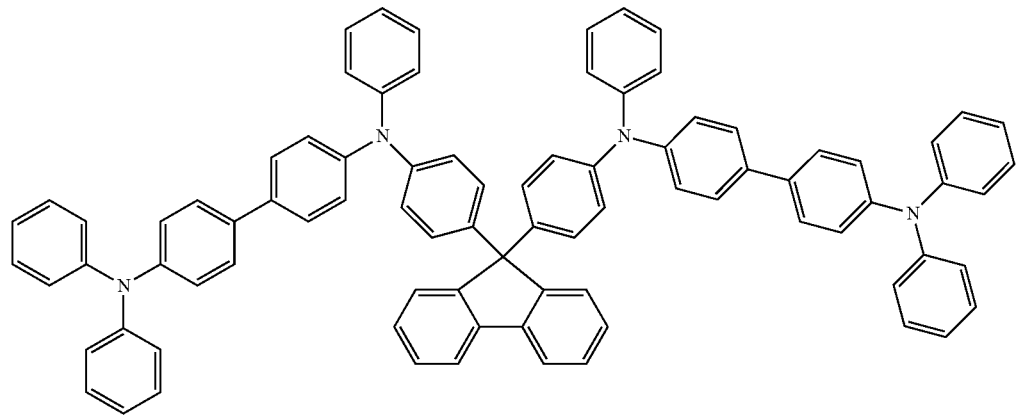
Specific examples of preferred compounds of the arylamine compound having two triphenylamine structures in its molecule, as represented by the foregoing general formula (3), which is suitably used for the organic EL device of the invention, are given below, but it should not be construed that the invention is limited to these compounds.
(3-1)
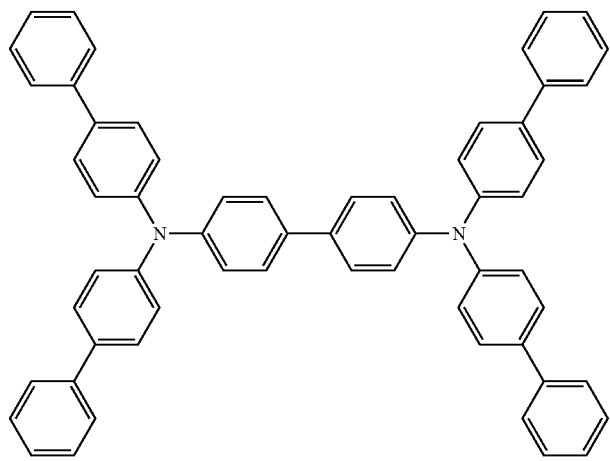

-continued
[Chem. 31]
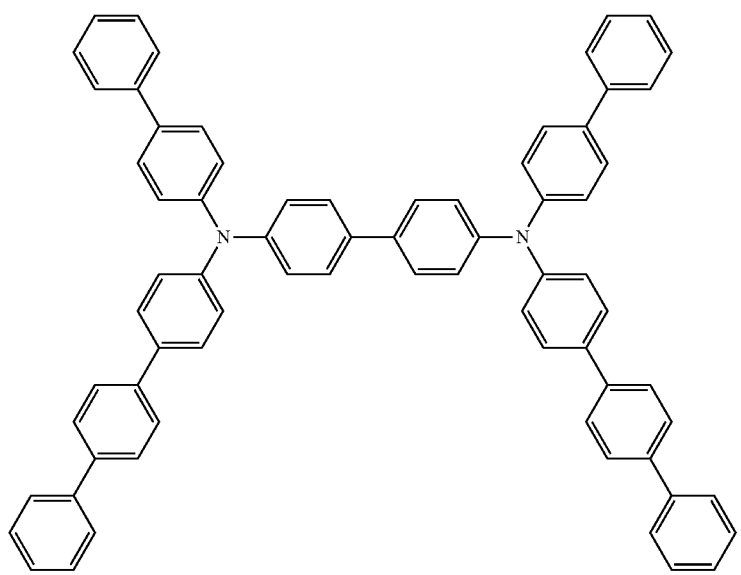
(3-2)
[Chem. 32]
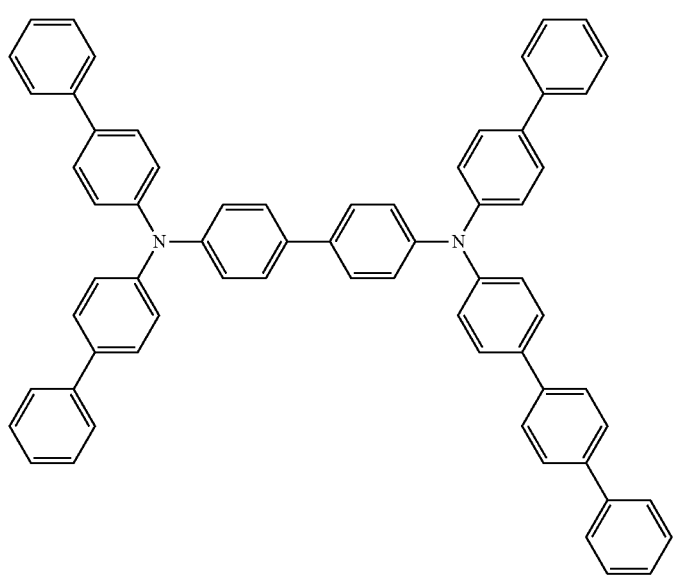
(3-3)

[Chem. 33]
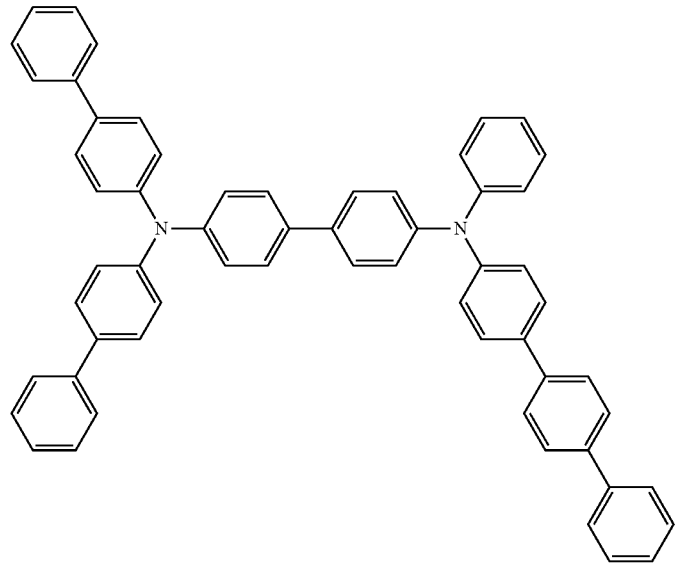
(3-4)
[Chem. 34]
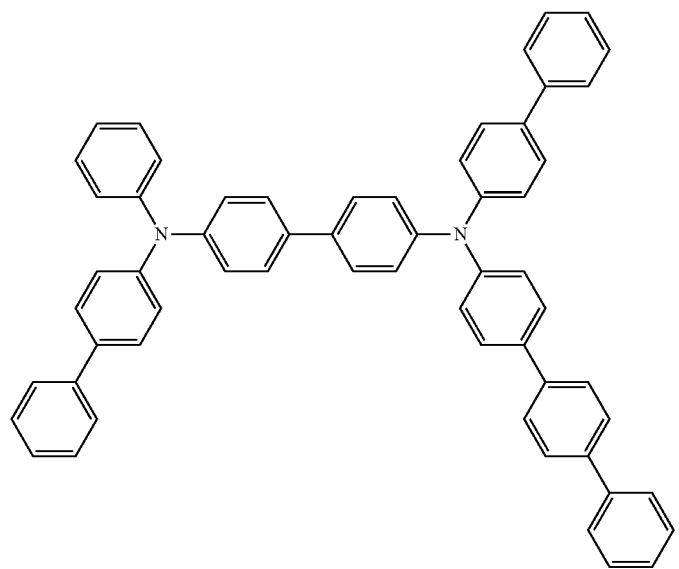
(3-5)

[Chem. 35]
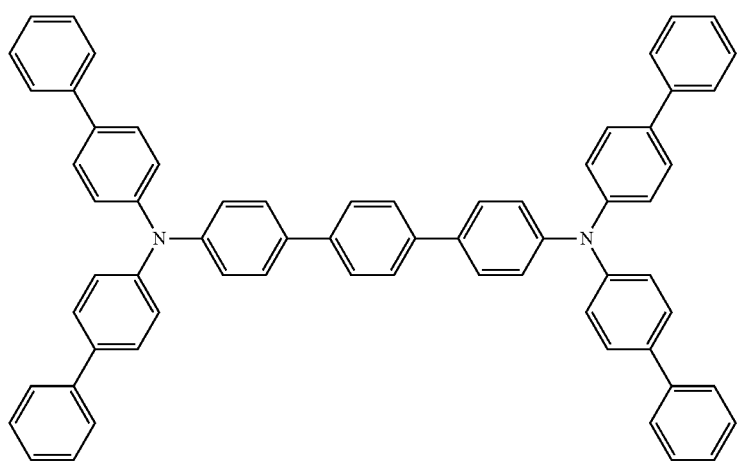
(3-6)
[Chem. 36]
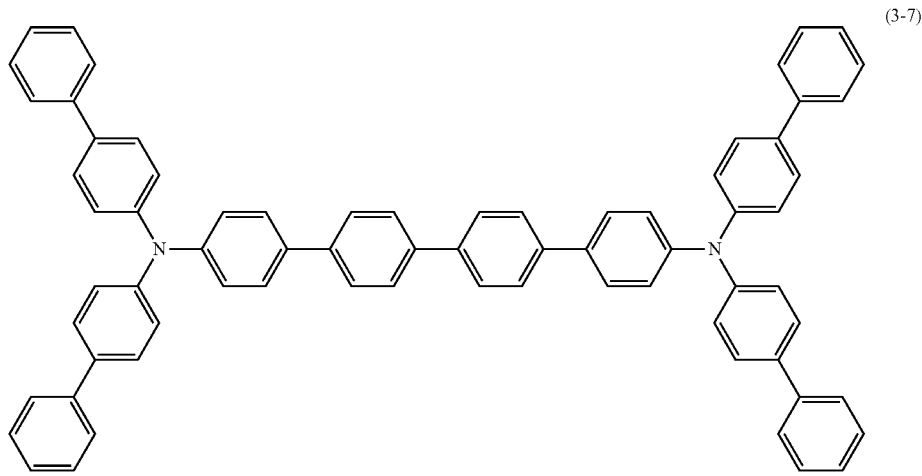
(3-7)
[Chem. 37]
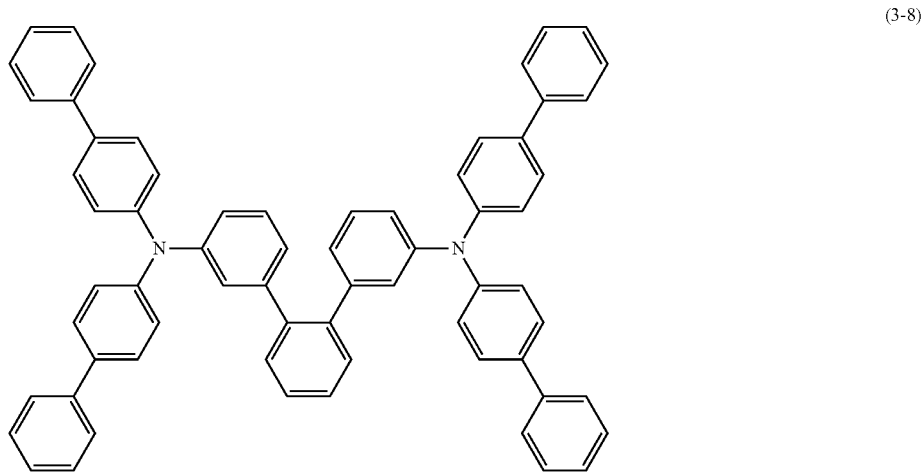
(3-8)

-continued
[Chem. 38]
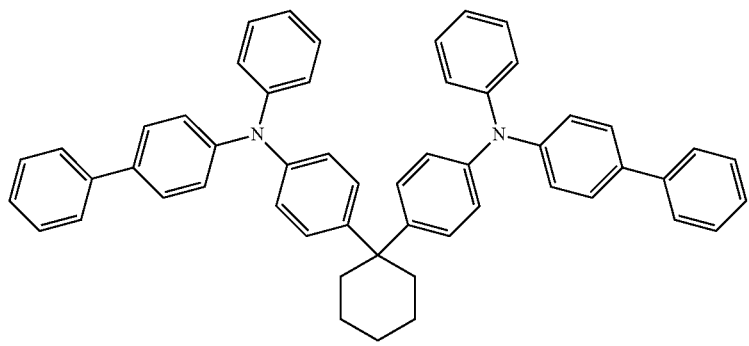
(3-9)
[Chem. 39]
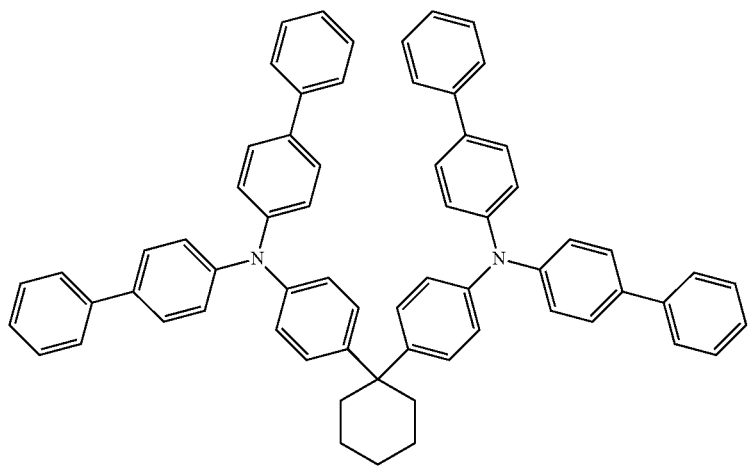
(3-10)
[Chem. 40]
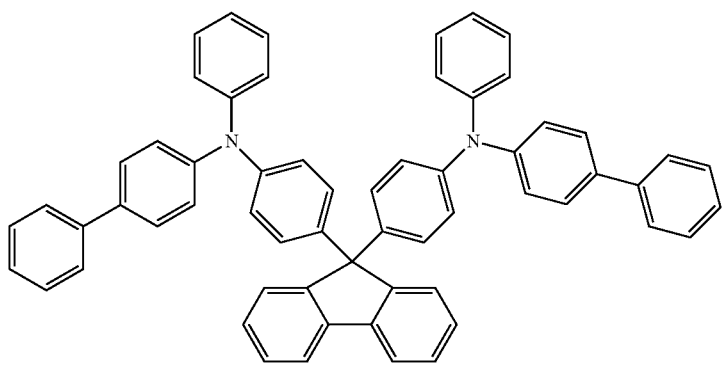
(3-11)

-continued
[Chem. 41]
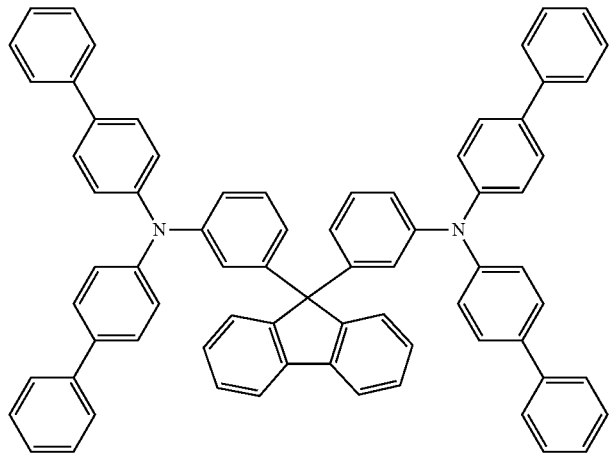
(3-12)
[Chem. 42]
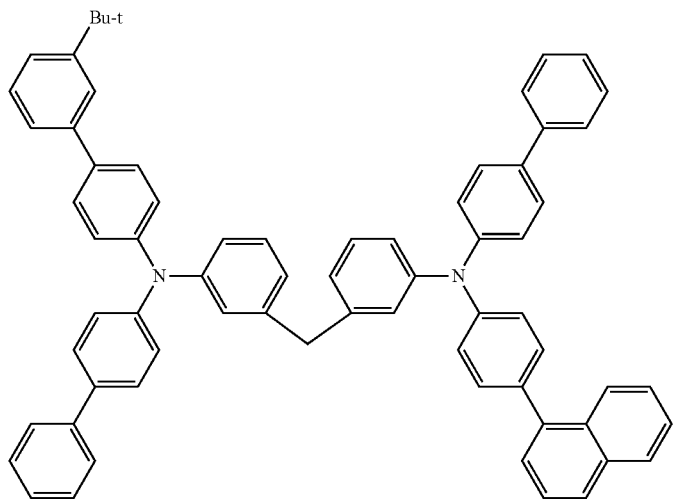
(3-13)
[Chem. 43]
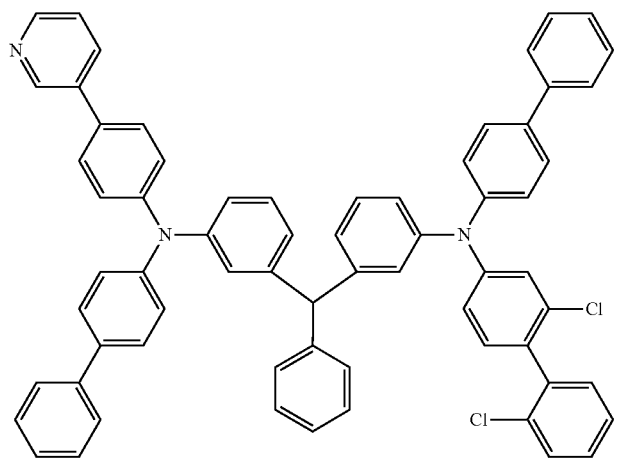
(3-14)

[Chem. 44]

(3-15)

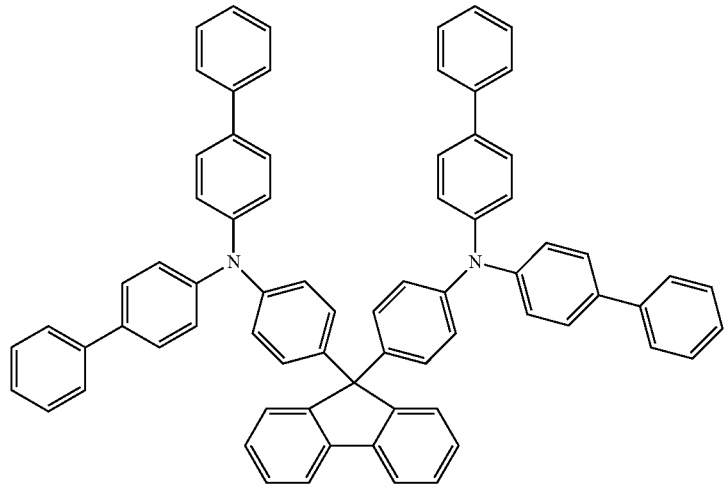

As the arylamine compound having two triphenylamine structures in its molecule which is suitably used for the organic EL device of the invention, the other specific examples than the arylamine compound having two triphenylamine structures in its molecule represented by the foregoing general formula (3) are given below, but it should not be construed that the invention is limited to these compounds.

[Chem. 45]

(3'-1)

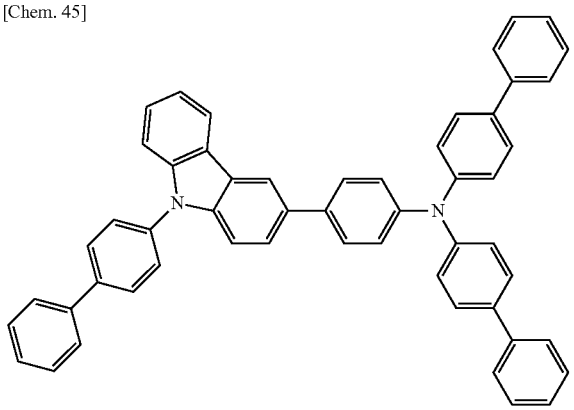

[Chem. 46]

(3'-2)

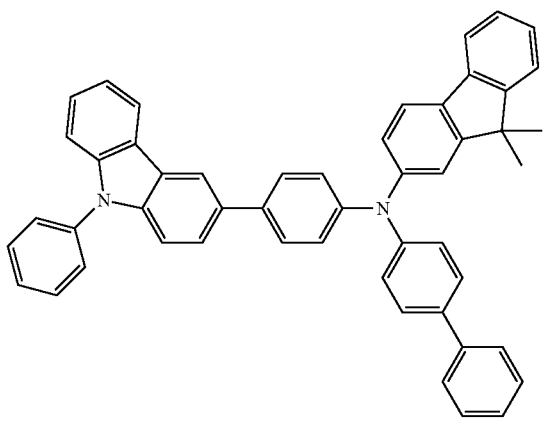

The compound having a pyridine ring and a pyridoindole ring in its molecule, as represented by the foregoing general formula (1), the foregoing general formula (4) or the foregoing general formula (5), which is used for the organic EL device of the invention, can be, for example, synthesized by subjecting a corresponding halogenoanilinopyridine to a cyclization reaction with a palladium catalyst to synthesize a pyridoindole ring (see, e.g., Non-Patent Document 3), and then condensing it with a halogenopyridine or one of various halogenoarylenes having a pyridyl group. The various halogenoarylenes having a bipyridyl group can be synthesized by condensing a corresponding aldehyde and acetylpyridine in the presence of a base and further allowing the condensed product to react with a corresponding pyridinium iodide (see, e.g., Non-Patent Document 4).

Also, the thus synthesized corresponding pyridoindole ring is subjected to a condensation reaction with one of various halogenoarylenes to synthesize a halogenoarylene pyridoindole ring structure, which is then subjected to a boronic acid esterification reaction with a palladium catalyst, whereby a corresponding boronic acid ester can be synthesized. Furthermore, a corresponding dihalogenopyridine derivative is subjected to a condensation reaction with a tin reagent to synthesize a dihalogenopyridyl group (see, e.g., Non-Patent Document 6), which is then subjected to a condensation reaction with the foregoing boronic acid ester, whereby a compound having a substituted pyridyl group and a pyridoindole ring structure connected through an arylene group can be synthesized.

Non-Patent Document 3: *J. Chem. Soc., Perkin Trans.* 1, p. 1505 (1999)

Non-Patent Document 4: *Synthesis*, 1 (1976)

Non-Patent Document 5: *J. Org. Chem.*, 67, p. 443 (2002)

The arylamine compound having, in its molecule, a structure in which three or more triphenylamine structures are connected through a single bond or a hetero atom-free divalent group, as represented by the foregoing general formula (2), or the arylamine compound having two triphenylamine structures in its molecule, as represented by the foregoing general formula (3), both of which arylamine compounds are used for the organic EL device of the invention, can be synthesized by known methods (see, e.g., Patent Documents 7 to 9).

Patent Document 7: JP-A-7-126615
Patent Document 8: JP-A-8-048656
Patent Document 9: JP-A-2005-108804

Specific examples of preferred compounds of the compound having a pyridine ring and a pyridoindole ring in its molecule, as represented by the foregoing general formula (1), which is used for the organic EL device of the invention, are given below, but it should not be construed that the invention is limited to these compounds.

[Chem. 47]

(1-1)

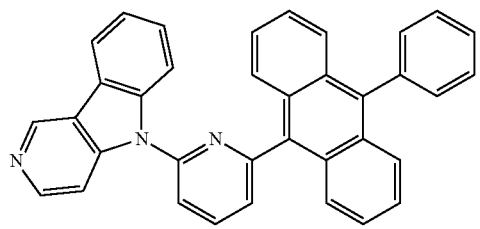

[Chem. 48]

(1-2)

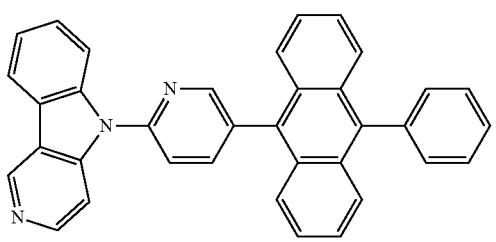

[Chem. 49]

(1-3)

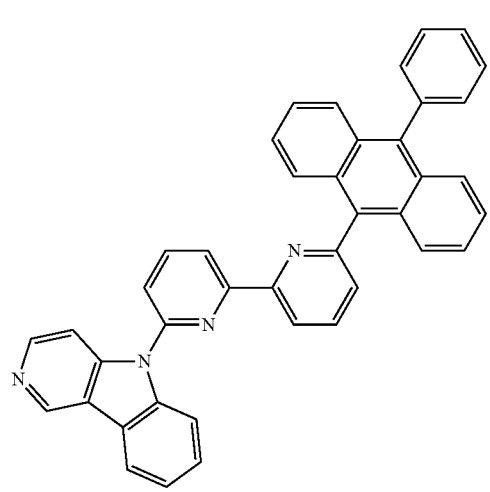

[Chem. 50]

(1-4)

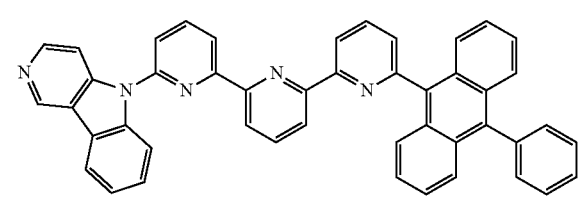

[Chem. 51]

(1-5)

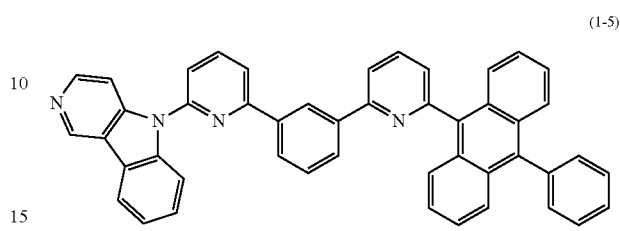

[Chem. 52]

(1-6)

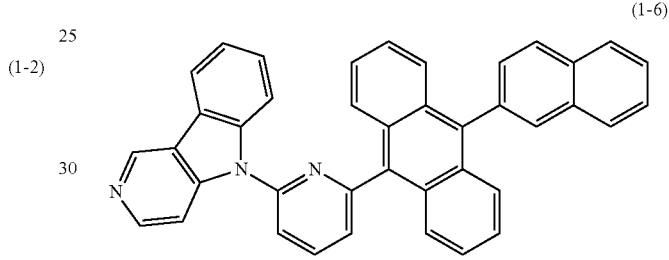

[Chem. 53]

(1-7)

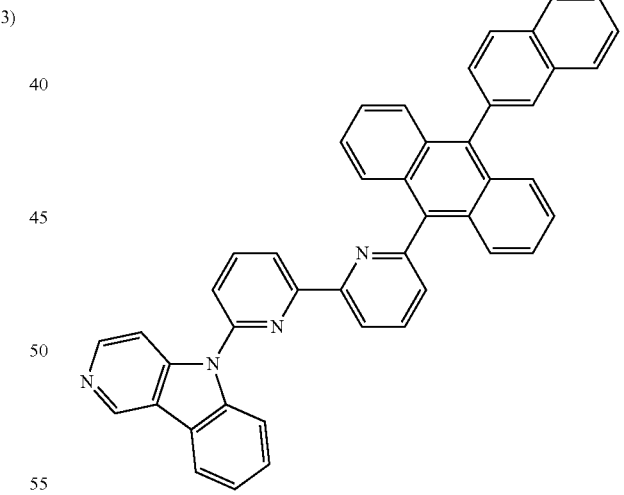

[Chem. 54]

(1-8)

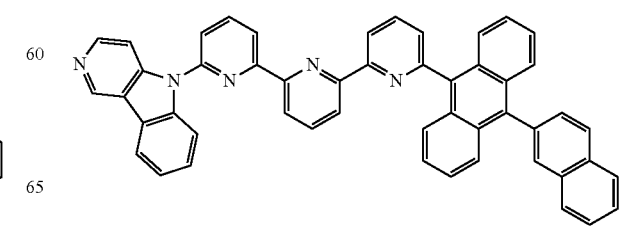

[Chem. 55]
(1-9)
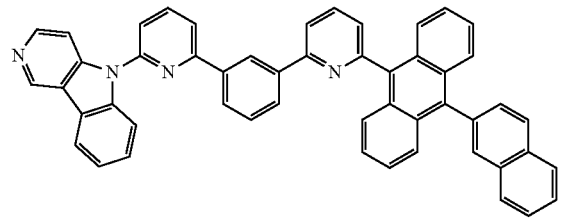
[Chem. 56]
(1-10)
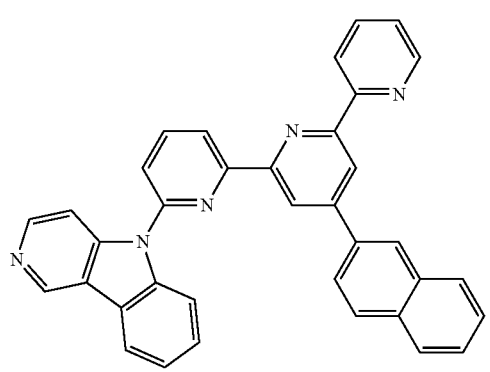
[Chem. 57]
(1-11)
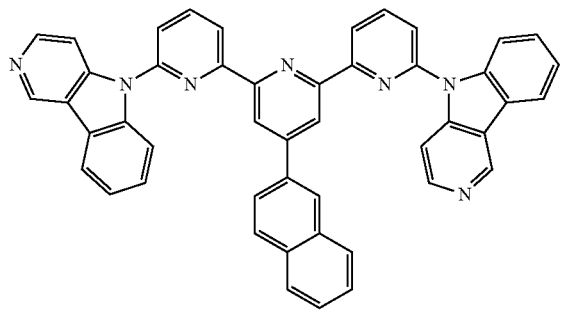
[Chem. 58]
(1-12)
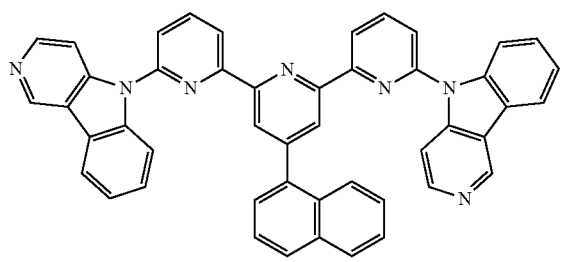
[Chem. 59]
(1-13)
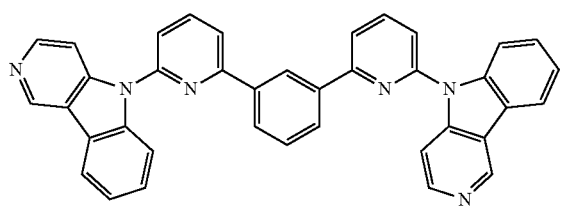
[Chem. 60]
(1-14)
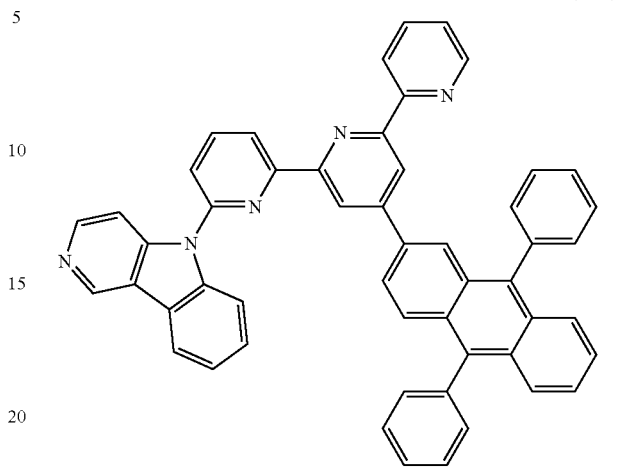
[Chem. 61]
(1-15)
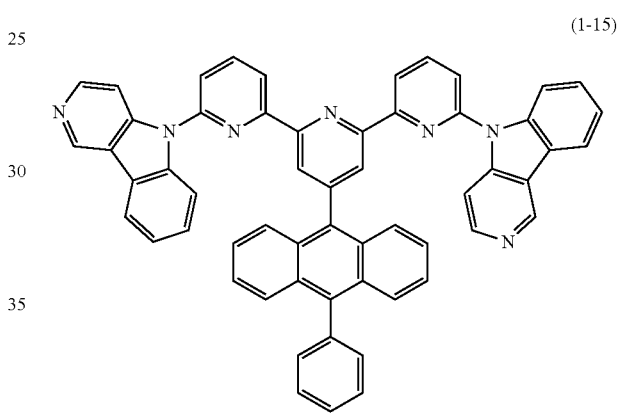
[Chem. 62]
(1-16)
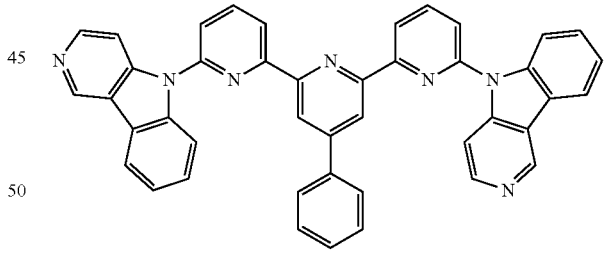
[Chem. 63]
(1-17)
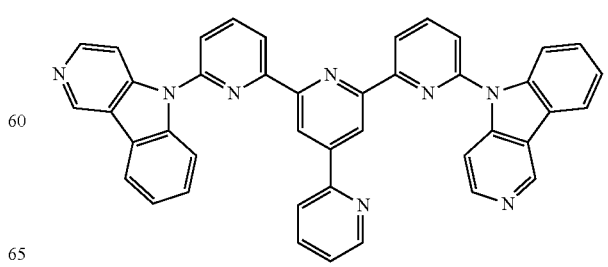

-continued
(1-18)
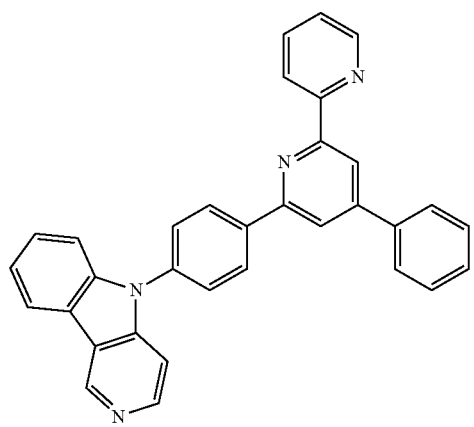
(1-19)
(1-20)
(1-21)
-continued
(1-22)
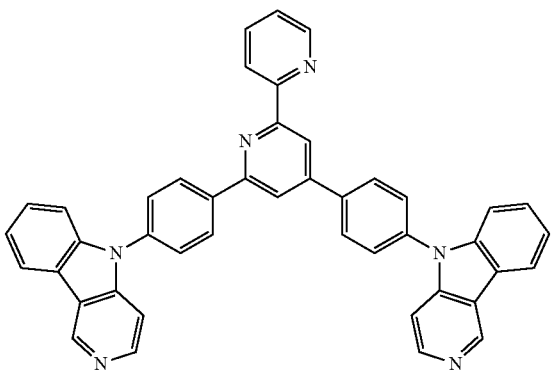
(1-23)
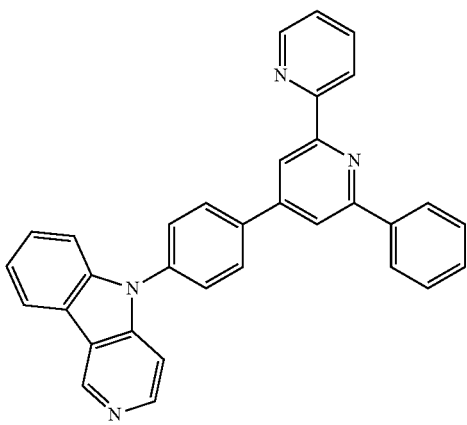
(1-24)
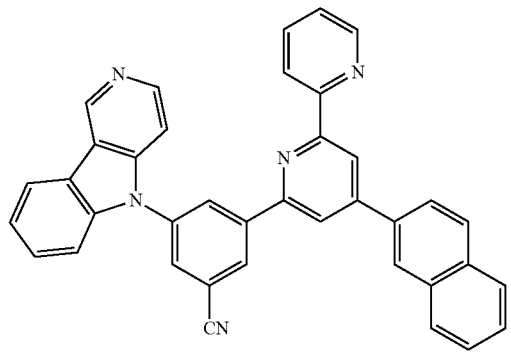

[Chem. 71]
(1-25)
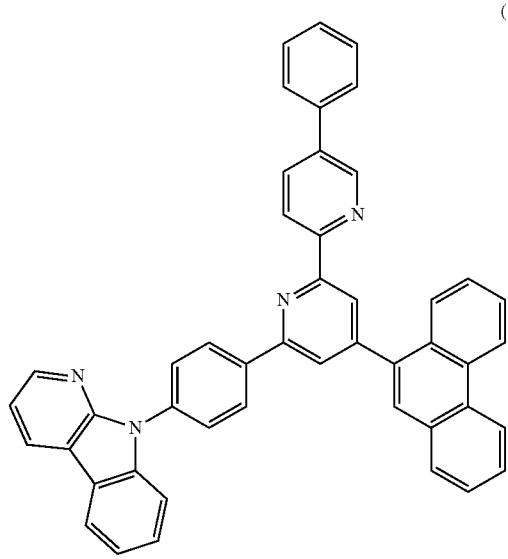
[Chem. 72]
(1-26)
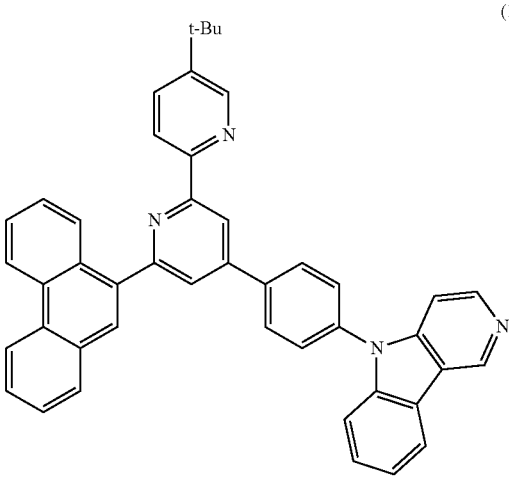
[Chem. 73]
(1-27)
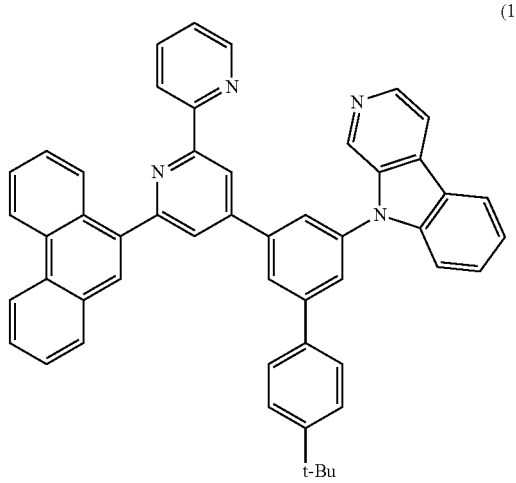
[Chem. 74]
(1-28)
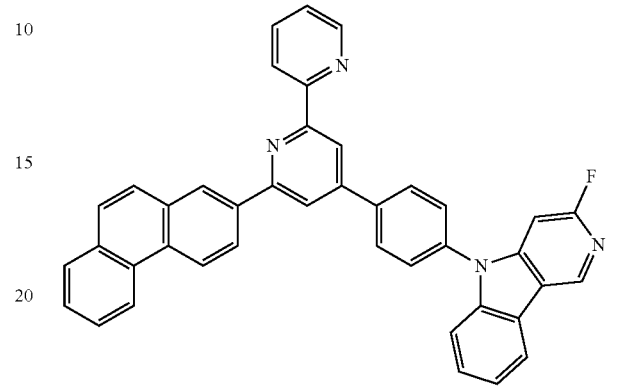
[Chem. 75]
(1-29)
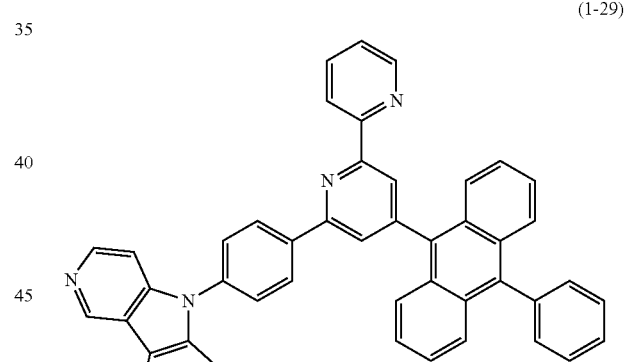
[Chem. 76]
(1-30)
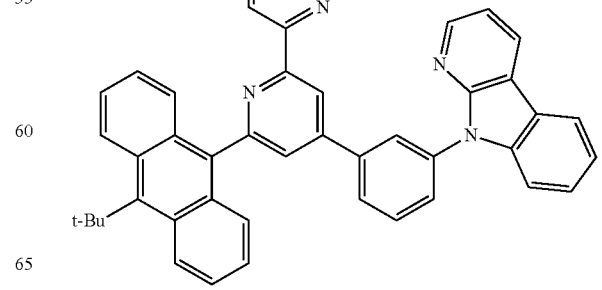

(1-31)
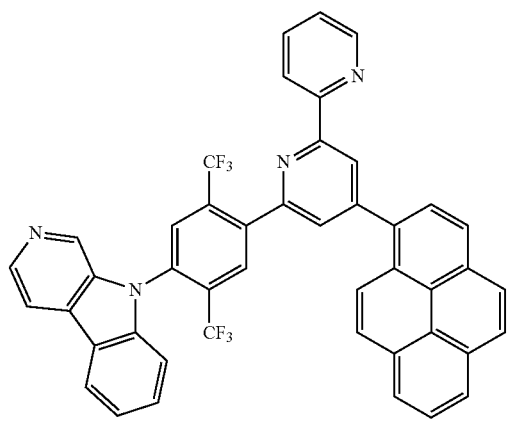
(1-34)
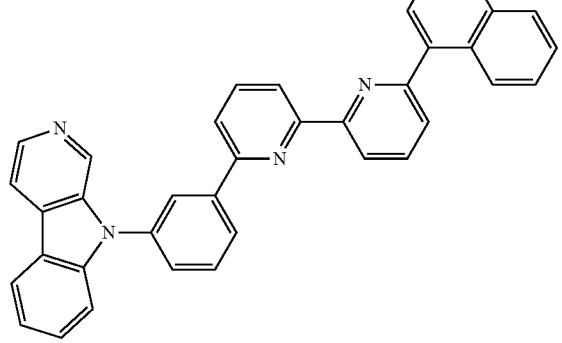
(1-32)
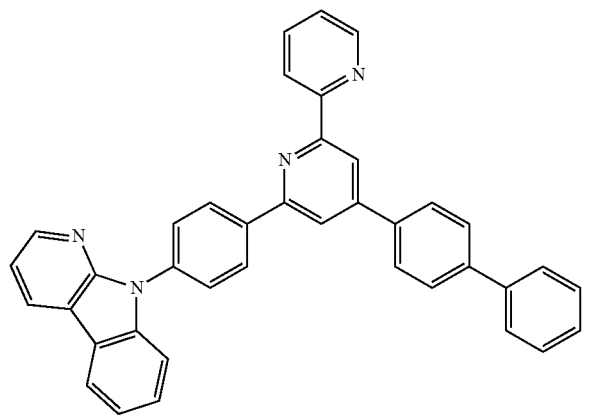
(1-35)
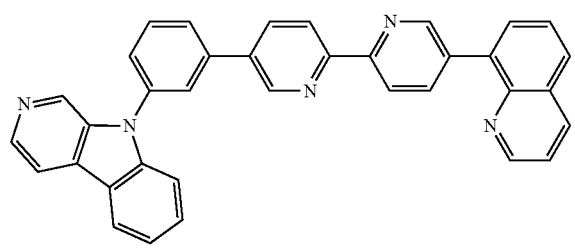
(1-33)
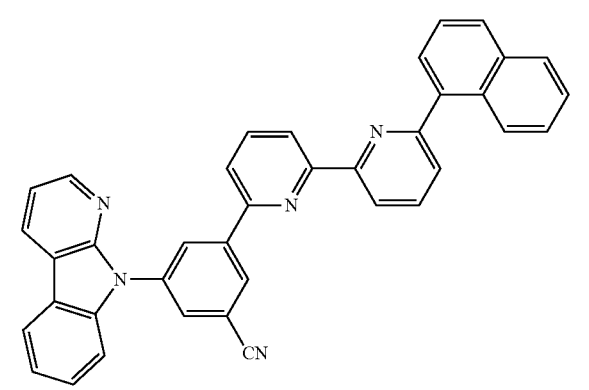
(1-36)
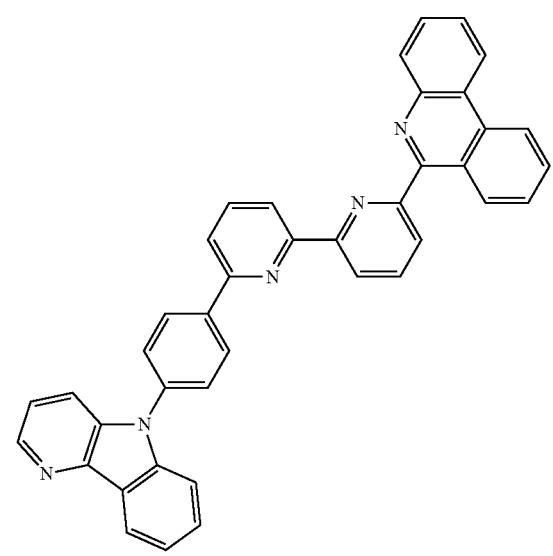

[Chem. 83]

(1-37)

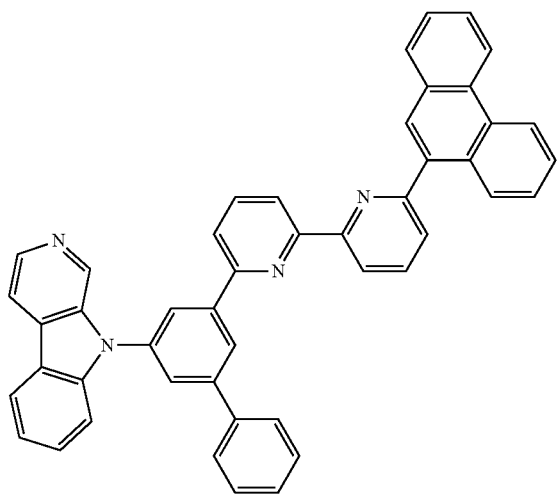

[Chem. 84]

(1-38)

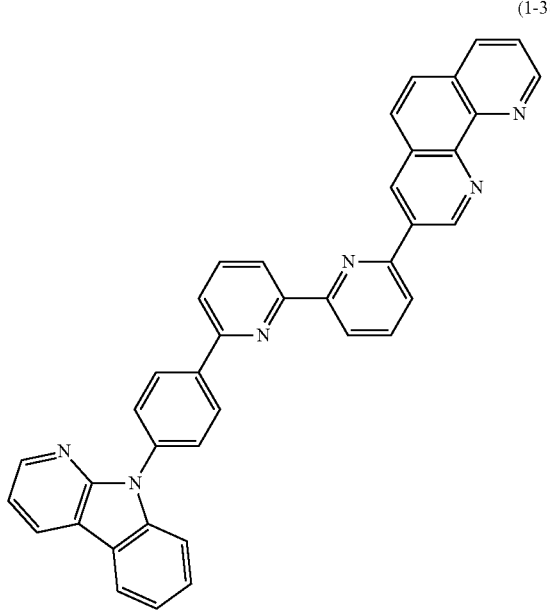

Figure 2:
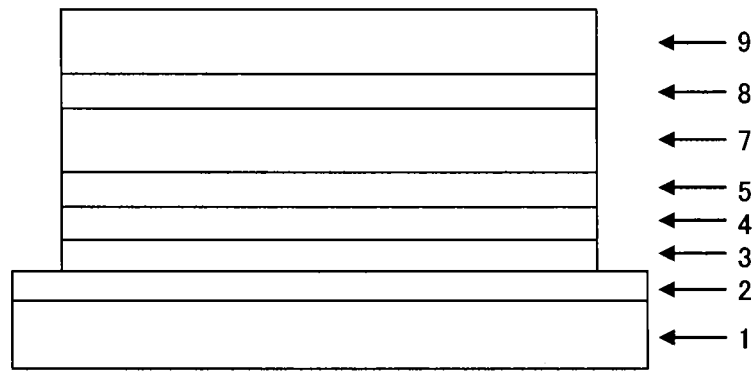
FIG. 2 is a view showing a configuration of an EL device of the Examples.

Examples of the structure of the organic EL device of the invention include a structure having an anode, a hole-injecting layer, a hole-transporting layer, an emitting layer, an electron-transporting layer, an electron-injection layer, and a cathode in this order on a substrate as shown in FIG. 2, and a structure further having a hole-blocking layer between the emitting layer and the electron-transporting layer. In these multilayer structure, it is possible to omit several layers of the organic layers and, for example, the structure may have a constitution sequentially having an anode, a hole-injection layer, a hole-transporting layer, an emitting layer, an electron-transporting layer, and cathode on a substrate.

As the anode of the organic EL device of the invention, an electrode material having a large work function, such as ITO or gold, is used.

As the hole-injecting layer, the arylamine compound having a high hole mobility and having, in its molecule, a structure in which three or more triphenylamine structures are connected through a single bond or a hetero atom-free divalent group is used.

As the hole-transporting layer, the arylamine compound having two triphenylamine structures in its molecule is used.

The hole-transporting layer is usually used in a film thickness of from 40 to 60 nm. However, in the organic EL device of the invention, even when the film thickness is 100 nm or more, a rise of the driving voltage is suppressed and the practical driving voltage can be kept in the film thickness of from 20 to 300 nm. In order to keep the practical driving voltage, the film thickness is more preferably from 20 to 200 nm.

As the emitting layer and the hole-blocking layer of the organic EL device of the invention, aluminum complexes, styryl derivatives, thiazole derivatives, oxazole derivatives, carbazole derivatives, polydialkylfluorene derivatives and the like are used.

Also, as the host material of the emitting layer, for example, a fluorescent material such as quinacridone, coumarin, rubrene can be used. A green phosphorescent material such as an iridium complex of phenylpyridine (Ir(PPy)$_3$); a blue phosphorescent material such as Firpic or Fir 6; a red phosphorescent material such as Btp2Ir (acac); and the like are used as a phosphorescent material. At that time, a high-performance organic EL device can also be prepared by using a hole-injecting/transporting host material 4,4'-di(N-carbazolyl)biphenyl (hereinafter referred to as "CBP") or the like as the host material.

As the hole-blocking layer of the organic EL device of the invention, phenanthroline derivatives such as BCP (bathocuproine), aluminum complexes such as BAlq (aluminum (III) bis(2-methyl-8-quinolinato)-4-phenylphenolate) and the like, each having a large value of ionization potential and a characteristic of blocking holes, can be used. Also, an electron-transporting material such as substituted bipyridyl compounds, thiazole derivatives, oxazole derivatives, oxadiazole derivatives, imidazole derivatives, carbazole derivatives and polydialkylfluorene derivatives can be used so far as it has a characteristic of blocking holes.

Alternatively, as the hole-blocking layer, the foregoing compound having a pyridine ring and a pyridoindole ring in its molecule can also be used.

As the electron-transporting layer of the organic EL device of the invention, it is preferable to use the foregoing compound having a pyridine ring and a pyridoindole ring in its molecule.

Alternatively, as the electron-transporting layer, substituted bipyridyl compounds, phenanthroline derivatives, aluminum complexes, thiazole derivatives, oxazole derivatives, oxadiazole derivatives, imidazole derivatives, carbazole derivatives, polydialkylfluorene derivatives and the like can be used.

The organic EL device of the invention may have an electron-injecting layer as shown in FIG. 1 and FIG. 2. As the electron-injecting layer, lithium fluoride or the like can be used.

As the cathode, an electrode material having a low work function such as aluminum, or an alloy having a lower work function such as aluminum magnesium is used as the electrode material.

EXAMPLES

Embodiments of the invention will be described in greater detail with reference to the following Examples, but the invention should not be construed as being limited to the following Examples so far as not exceeding the gist thereof.

Example 1A

An organic EL device was prepared by depositing a hole-injecting layer 3, a hole-transporting layer 4, an emitting layer 5, an electron-transporting layer 7, an electron-injecting layer 8 and a cathode (aluminum electrode) 9 in this order on a glass substrate 1 on which an ITO electrode had been formed as a transparent anode 2 in advance, as shown in FIG. 2.

First of all, after the glass substrate 1 on which ITO having a film thickness of 150 nm had been formed was ultrasonically washed in isopropyl alcohol for 20 minutes, it was washed by boiling on a hot plate heated at 150° C. for 20 minutes. Thereafter, this ITO-provided glass substrate was mounted in a vacuum deposition machine and subjected to an oxygen plasma treatment for 5 minutes, following by evacuating to 0.001 Pa or lower.

Subsequently, Compound 2-1 of the following structural formula was formed in a film thickness of 20 nm as the hole-injecting layer 3 so as to cover the transparent electrode 2. On this hole-injecting layer 3, Compound 3-1 of the following structural formula was formed in a film thickness of 40 nm as the hole-transporting layer 4. On this hole-transporting layer 4, Compound 7 of the following structural formula and Compound 8 of the following structural formula were subjected to two-component deposition in a film thickness of 30 nm as the emitting layer 5 at a deposition rate such that a deposition rate ratio of Compound 7 to Compound 8 was 5/95. On this emitting layer 5, Alq$_3$ was formed in a film thickness of 30 nm as the electron-transporting layer 7. On this electron-transporting layer 7, lithium fluoride was formed in a film thickness of 0.5 nm as the electron-injecting layer 8. Finally, aluminum was deposited in a thickness of 150 nm to form the cathode 9.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.43 V.

[Compound 85]

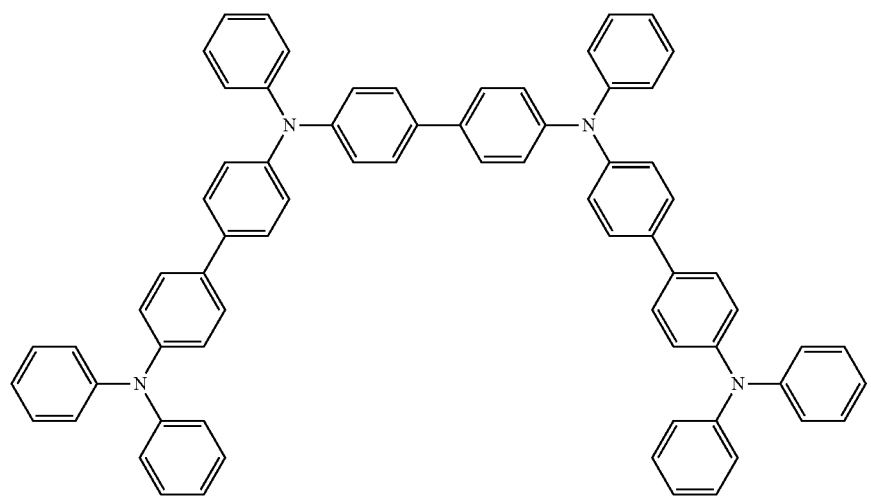

(2-1)

[Compound 86]

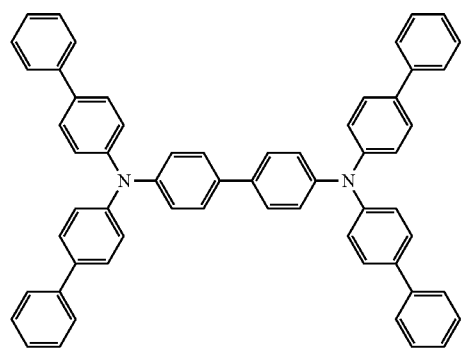

(3-1)

[Compound 87]

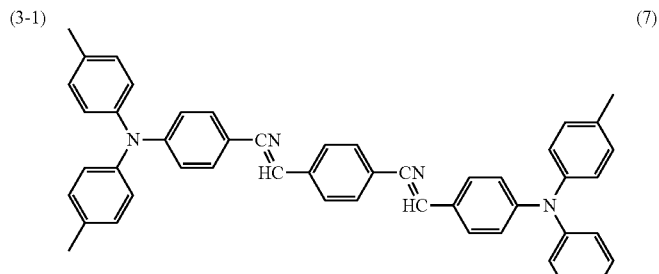

(7)

Compound 88]

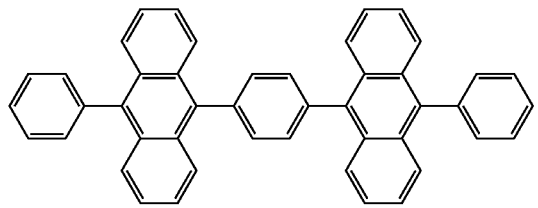

(8)

Example 2A

An organic EL device was prepared in the same manner as in Example 1A except that Compound 3-1 was formed in a film thickness of 100 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.45 V.

Example 3A

An organic EL device was prepared in the same manner as in Example 1A except that Compound 3-1 was formed in a film thickness of 150 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.65 V.

Example 4A

An organic EL device was prepared in the same manner as in Example 1A except that Compound 3-1 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.70 V.

Example 5A

An organic EL device was prepared in the same manner as in Example 1A except that Compound 3-1 was formed in a film thickness of 300 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 7.41 V.

Example 6A

An organic EL device was prepared in the same manner as in Example 1A except that Compound 2-4 of the following structural formula was formed in a film thickness of 20 nm as the hole-injecting layer 3 in placed of Compound 2-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.49 V.

[Compound 89]

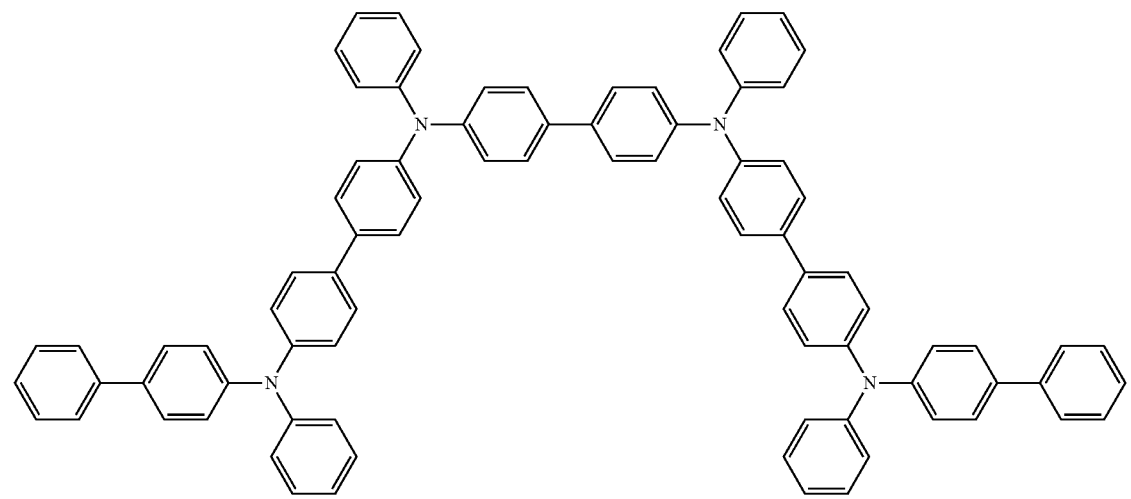

(2-4)

Example 7A

An organic EL device was prepared in the same manner as in Example 6A except that Compound 3-1 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.79 V.

Example 8A

An organic EL device was prepared in the same manner as in Example 1A except that Compound 2-6 of the following structural formula was formed in a film thickness of 20 nm as the hole-injecting layer 3 in placed of Compound 2-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.63 V.

[Compound 90]

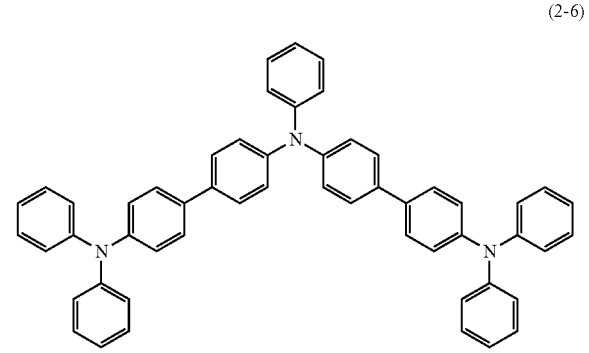

(2-6)

Example 9A

An organic EL device was prepared in the same manner as in Example 8A except that Compound 3-1 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.91 V.

Example 10A

An organic EL device was prepared in the same manner as in Example 1A except that Compound 2-10 of the following structural formula was formed in a film thickness of 20 nm as the hole-injecting layer 3 in placed of Compound 2-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.59 V.

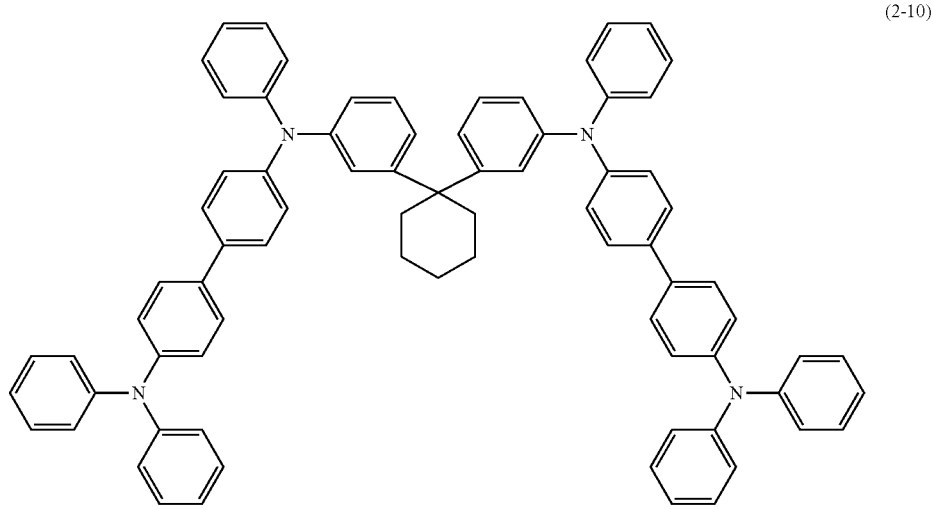

(2-10)

Example 11A

An organic EL device was prepared in the same manner as in Example 10A except that Compound 3-1 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.89 V.

Example 12A

An organic EL device was prepared in the same manner as in Example 1A except that Compound 2-14 of the following structural formula was formed in a film thickness of 20 nm as the hole-injecting layer 3 in placed of Compound 2-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.56 V.

[Compound 92]

(2-14)

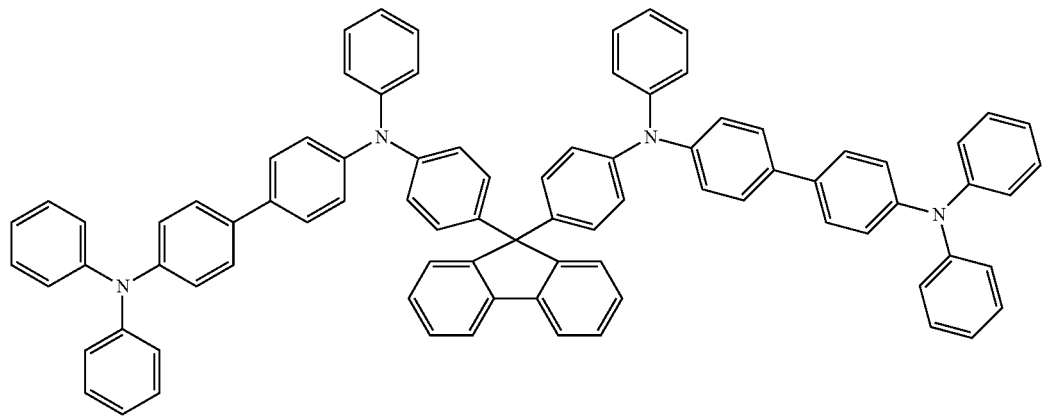

Example 13A

An organic EL device was prepared in the same manner as in Example 12A except that Compound 3-1 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.88 V.

Example 14A

An organic EL device was prepared in the same manner as in Example 1A except that Compound 3-4 of the following structural formula was formed in a film thickness of 40 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.44 V.

[Compound 93]

(3-4)

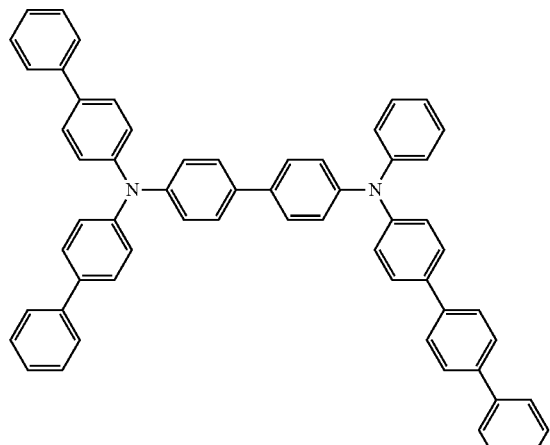

Example 15A

An organic EL device was prepared in the same manner as in Example 14A except that Compound 3-4 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.73 V.

Example 16A

An organic EL device was prepared in the same manner as in Example 1A except that Compound 3-6 of the following structural formula was formed in a film thickness of 40 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.54 V.

[Compound 94]

(3-6)

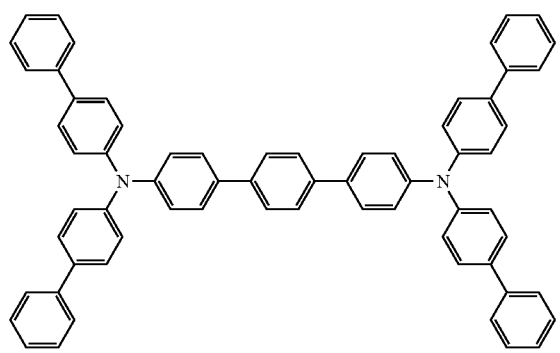

Example 17A

An organic EL device was prepared in the same manner as in Example 16A except that Compound 3-6 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.85 V.

[Compound 95]

Example 18A

An organic EL device was prepared in the same manner as in Example 1A except that Compound 3-10 of the following structural formula was formed in a film thickness of 40 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.51 V.

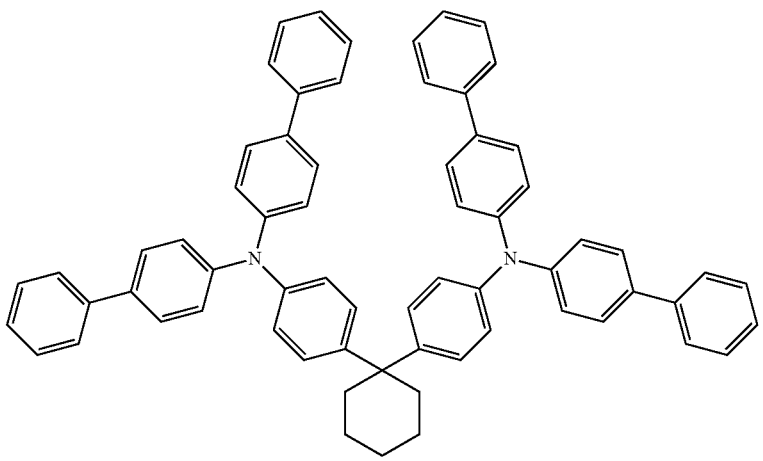

(3-10)

Example 19A

An organic EL device was prepared in the same manner as in Example 18A except that Compound 3-10 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.82 V.

Example 20A

An organic EL device was prepared in the same manner as in Example 1A except that Compound 3-15 of the following structural formula was formed in a film thickness of 40 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.46 V.

[Compound 96]

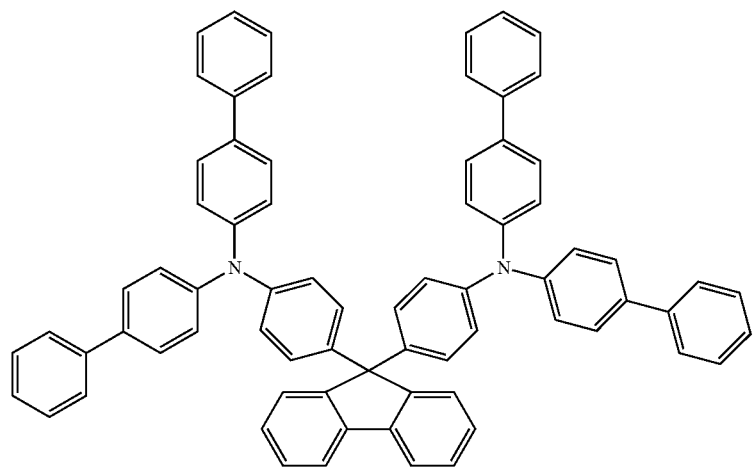

(3-15)

Example 21A

An organic EL device was prepared in the same manner as in Example 20A except that Compound 3-15 was formed in a film thickness of 200 nm as the hole-transporting layer 4.

The thus prepared organic EL device was measured for characteristics upon being applied with a direct current voltage at ordinary temperature in the air. As a result, a driving voltage at the time of flowing of a current with a current density of 10 mA/cm$^2$ was found to be 6.76 V.

Comparative Example 1A

An organic EL device was prepared in the same manner as in Example 1A except that CuPc was formed in a film thickness of 20 nm as the hole-injecting layer 3 in placed of Compound 2-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 8.30 V.

Comparative Example 2A

An organic EL device was prepared in the same manner as in Example 1A except that Compound 9 of the following structural formula was formed in a film thickness of 20 nm as the hole-injecting layer 3 in placed of Compound 2-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 8.14 V.

[Compound 97]

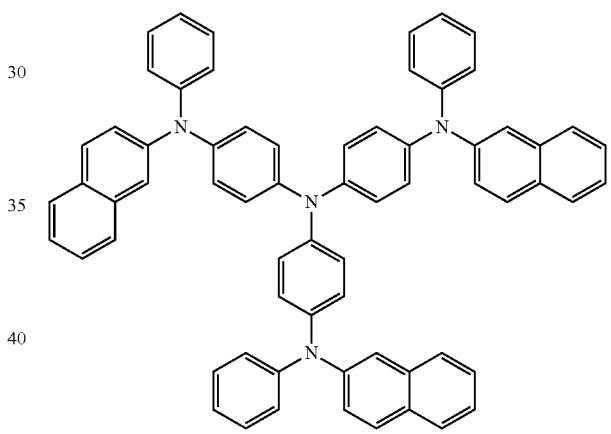

(9)

Comparative Example 3A

An organic EL device was prepared in the same manner as in Example 1A except that NPD was formed in a film thickness of 40 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm$^2$ was found to be 5.50 V.

Comparative Example 4A

An organic EL device was prepared in the same manner as in Example 1A except that NPD was formed in a film thickness of 100 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm² was found to be 6.30 V.

Comparative Example 5A

An organic EL device was prepared in the same manner as in Example 3A except that NPD was formed in a film thickness of 150 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm² was found to be 7.55 V.

Comparative Example 6A

An organic EL device was prepared in the same manner as in Example 4A except that NPD was formed in a film thickness of 200 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm² was found to be 8.95 V.

Comparative Example 7A

An organic EL device was prepared in the same manner as in Example 5A except that NPD was formed in a film thickness of 300 nm as the hole-transporting layer 4 in placed of Compound 3-1.

The thus prepared organic EL device was measured for characteristics upon being applied with a direct current voltage at ordinary temperature in the air. As a result, a driving voltage at the time of flowing of a current with a current density of 10 mA/cm² was found to be 11.1 V.

From Example 1A and Comparative Example 1A, when the compound of the hole-injecting layer was replaced from CuPc to Compound 2-1, the driving voltage was lowered from 8.30 V to 5.43 V. Also, from Example 1A and Comparative Example 2A, when the compound of the hole-injecting layer was replaced from Compound 9 of the foregoing structural formula to Compound 2-1, the driving voltage was lowered from 8.14 V to 5.43 V.

According to the organic EL devices of the invention, it was found that the carrier balance of the inside of the organic EL device is improved through a combination of the specified two kinds of arylamine compounds and that as compared with the conventional organic EL devices using CuPc or Compound 9 of the foregoing structural formula, an organic EL device having a low driving voltage and a long life can be realized.

Furthermore, it could be confirmed from the comparison between Examples 1A to 5A and Comparative Examples 3A to 7A that in the case of using Compound 2-1 as the material of the hole-transporting layer, even when the film thickness of the hole-transporting layer is made thick, a reduction of the driving voltage is kept.

According to the organic EL devices of the invention, it was found that the carrier balance of the inside of the organic EL device is improved through a combination of the specified two kinds of arylamine compounds and that as compared with the conventional organic EL devices using NPD as a hole-transporting agent which is in general widely used, an organic EL device having a thick-film thickness hole-transporting layer with a low driving voltage and a long life can be realized.

Example 1B

Synthesis of [6-(4-5H-pyrido[4,3-b]indol-5-yl)phenyl]-4-napthalen-2-yl-[2,2']bipyridine (Compound 1-20)

To 10.0 g of 4'-bromoacetophenone were added 12.8 g of iodine and 80 mL of pyridine and heated, and the mixture was stirred at 100° C. for 3 hours. After cooling to room temperature, 100 mL of water was added, and purification was performed by recrystallization. Drying was performed under reduced pressure at 70° C. for 12 hours to give 15.5 g (yield: 76%) of 4-bromophenacylpyridinium iodide as a brown powder.

Subsequently, to 6.0 g of 2-naphthoaldehyde were added 4.7 g of 2-acetylpyridine and 40 mL of methanol, and the mixture was cooled to −5° C. while stirring. To the mixture, 62 mL of a 3 wt % NaOH/methanol solution was added dropwise, and the mixture was stirred at −5° C. for 2 hours. Thereafter, the reaction was further carried out at the same temperature for 2 days. To the reaction solution, 37.0 g of ammonium acetate, 15.5 g of the foregoing 4-bromophenacylpyridinium iodide and 100 mL of methanol were added, and the mixture was stirred at 55° C. for 2 days. After cooling to room temperature, the resulting crude product was collected by filtration and washed with methanol. Drying was performed under reduced pressure at 70° C. for 12 hours to give 3.8 g (yield: 23%) of 6-(4-bromophenyl)-4-naphthalen-2-yl-[2,2']bipyridine as a gray powder.

To 2.5 g of the obtained 6-(4-bromophenyl)-4-naphthalen-2-yl-[2,2']bipyridine were added 1.0 g of 5H-pyrido[4,3-b]indole, 0.2 g of a copper powder, 2.4 g of potassium carbonate, 0.2 mL of dimethyl sulfoxide and 10 mL of n-dodecane, and the mixture was stirred for 7 hours under refluxing. After cooling to room temperature, 60 mL of chloroform was added thereto, an insoluble matter was removed by filtration, and the filtrate was concentrated under reduced pressure to give a crude product. The crude product was purified by column chromatography (carrier: NH silica gel, eluent: hexane/chloroform) to give 1.85 g (yield: 62%) of [6-(4-5H-pyrido[4,3-b]indol-5-yl)phenyl]-4-naphthalen-2-yl-[2,2']bipyridine (Compound 1-20) as a white powder.

Synthesis Referential Example 1

Synthesis of (6"-naphthalen-1-yl-6-5H-pyrido[4,3-b]indol-5-yl-[2,2';6',2"]terpyridine To 0.9 g of 6"-boromo-6-5H-pyrido[4,3-b]indol-5-yl-[2,2';6',2"]terpyridine were added 0.39 g of naphthaleneboronic acid, 9 mL of a 2M potassium carbonate aqueous solution, 0.1 g of tetrakistriphenyl phosphine palladium(0), 120 mL of toluene and 30 mL of ethanol, and the mixture was stirred for 6 hours under refluxing. After cooling to room temperature, 200 mL of water was added and extraction was performed with 150 mL of chloroform. After drying over magnesium sulfate, the resultant was concentrated under reduced pressure to give a crude product. The crude product was purified by column chromatography (carrier: NH silica gel, eluent: chloroform) to give 799 mg (yield: 80%) of 6"-naphthalen-1-yl-6-5H-pyrido[4,3-b]indol-5-yl-

[2,2';6',2"]terpyridine (Compound 6) of the following structural formula as a white powder.

[Compound 98]

(6)

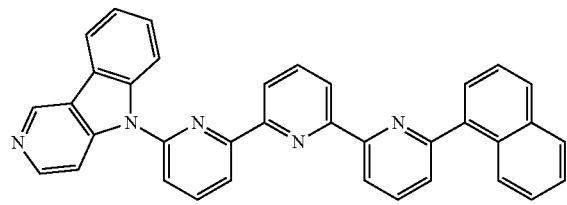

Example 2B

An organic EL device was prepared by depositing a hole-injecting layer 3, a hole-transporting layer 4, an emitting layer 5, an electron-transporting layer 7, an electron-injecting layer 8 and a cathode (aluminum electrode) 9 in this order on a glass substrate 1 on which an ITO electrode had been formed as a transparent anode 2 in advance, as shown in FIG. 2.

First of all, after the glass substrate 1 on which ITO having a film thickness of 150 nm had been formed was ultrasonically washed in isopropyl alcohol for 20 minutes, it was washed by boiling on a hot plate heated at 150° C. for 20 minutes. Thereafter, this ITO-provided glass substrate was mounted in a vacuum deposition machine and subjected to an oxygen plasma treatment for 5 minutes, following by evacuating to 0.001 Pa or lower.

Subsequently, Compound 2-1 of the following structural formula was formed in a film thickness of 20 nm as the hole-injecting layer 3 so as to cover the transparent electrode 2. On this hole-injecting layer 3, Compound 3-1 of the following structural formula was formed in a film thickness of 40 nm as the hole-transporting layer 4. On this hole-transporting layer 4, Compound 7 of the following structural formula and Compound 8 of the following structural formula were subjected to two-component deposition in a film thickness of 30 nm as the emitting layer 5 at a deposition rate such that a deposition rate ratio of Compound 7 to Compound 8 was 5/95. On this emitting layer 5, Compound 1-3 of the following structural formula was formed in a film thickness of 30 nm as the electron-transporting layer 7. On this electron-transporting layer 7, lithium fluoride was formed in a film thickness of 0.5 nm as the electron-injecting layer 8. Finally, aluminum was deposited in a thickness of 150 nm to form the cathode 9. The thus prepared organic EL device was measured for characteristics at ordinary temperature in the air.

The results of measuring the luminescence characteristics upon applying a direct current voltage to the prepared organic EL device are summarized and shown in Table 1.

[Compound 99]

(2-1)

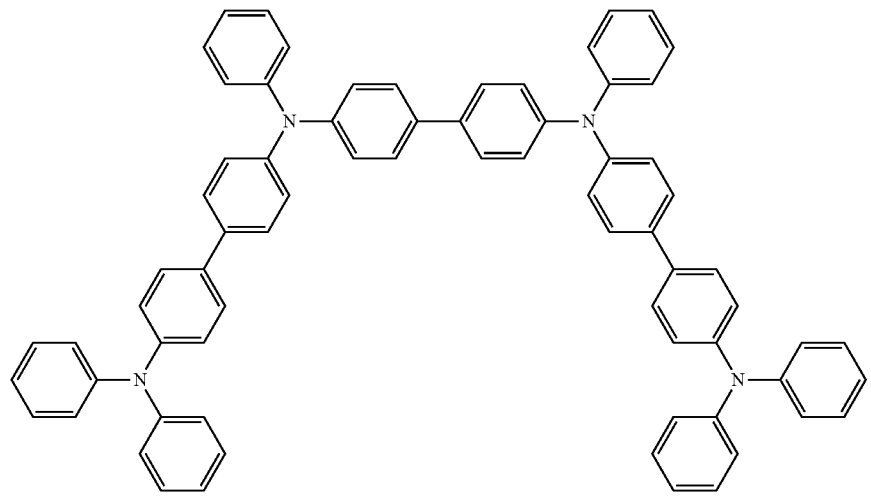

[Compound 100]

(3-1)

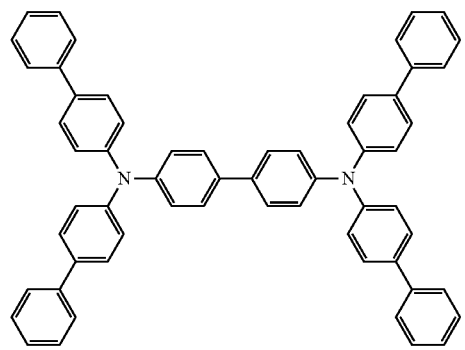

[Compound 101]

(7)

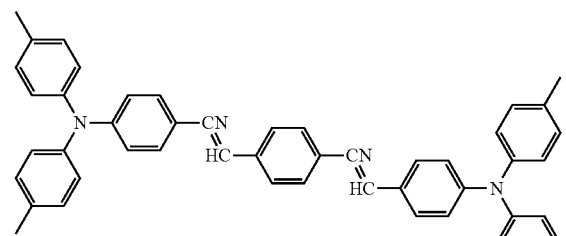

Compound 102]

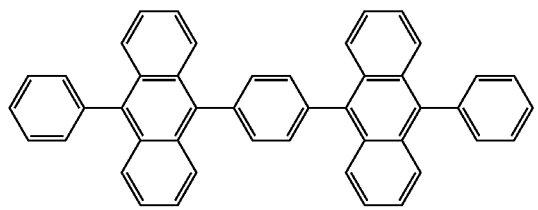
(8)

Compound 103]

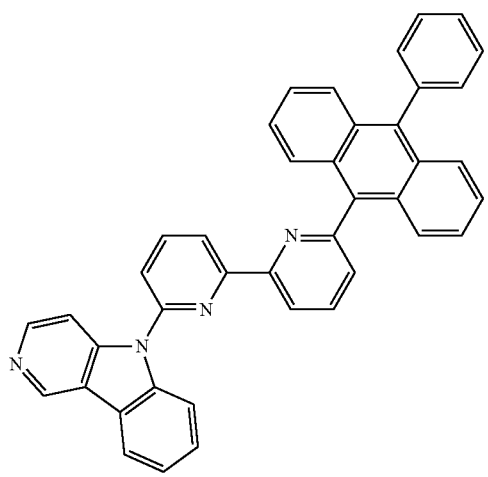
(1-3)

Example 3B

An organic EL device was prepared in the same manner as in Example 2B except that Compound 1-4 of the following structural formula was formed in a film thickness of 30 nm as the electron-transporting layer 7 in placed of Compound 1-3. The thus prepared organic EL device was measured for characteristics at ordinary temperature in the air.

The results of measuring the luminescence characteristics upon applying a direct current voltage to the prepared organic EL device are summarized and shown in Table 1.

[Compound 104]

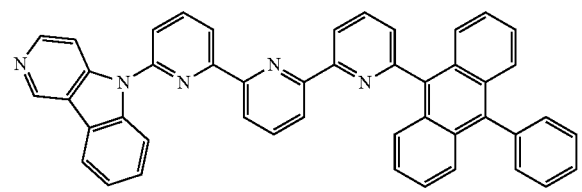
(1-4)

Example 4B

An organic EL device was prepared in the same manner as in Example 2B except that Compound 1-10 of the following structural formula was formed in a film thickness of 30 nm as the electron-transporting layer 7 in placed of Compound 1-3. The thus prepared organic EL device was measured for characteristics at ordinary temperature in the air.

The results of measuring the luminescence characteristics upon applying a direct current voltage to the prepared organic EL device are summarized and shown in Table 1.

[Compound 105]

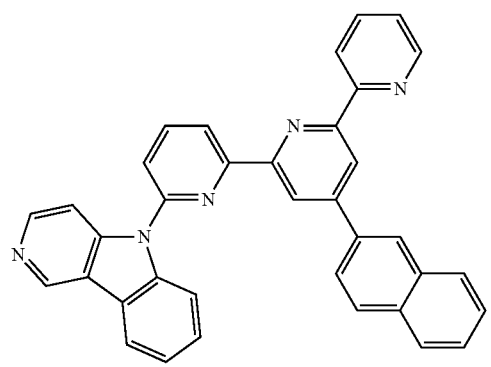
(1-10)

Example 5B

An organic EL device was prepared in the same manner as in Example 2B except that Compound 1-20 of the following structural formula was formed in a film thickness of 30 nm as the electron-transporting layer 7 in placed of Compound 1-3. The thus prepared organic EL device was measured for characteristics at ordinary temperature in the air.

The results of measuring the luminescence characteristics upon applying a direct current voltage to the prepared organic EL device are summarized and shown in Table 1.

[Compound 106]

(1-20)

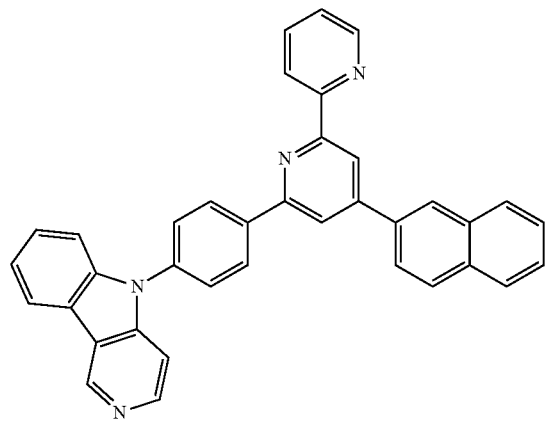

Example 6B

An organic EL device was prepared in the same manner as in Example 4B except that Compound 2-4 of the following structural formula was formed in a film thickness of 20 nm as the hole-injecting layer 3 in placed of Compound 2-1. The thus prepared organic EL device was measured for characteristics at ordinary temperature in the air.

The results of measuring the luminescence characteristics upon applying a direct current voltage to the prepared organic EL device are summarized and shown in Table 2.

Example 7B

An organic EL device was prepared in the same manner as in Example 4B except that Compound 2-6 of the following structural formula was formed in a film thickness of 20 nm as the hole-injecting layer 3 in placed of Compound 2-1. The thus prepared organic EL device was measured for characteristics at ordinary temperature in the air.

The results of measuring the luminescence characteristics upon applying a direct current voltage to the prepared organic EL device are summarized and shown in Table 2.

[Compound 108]

(2-6)

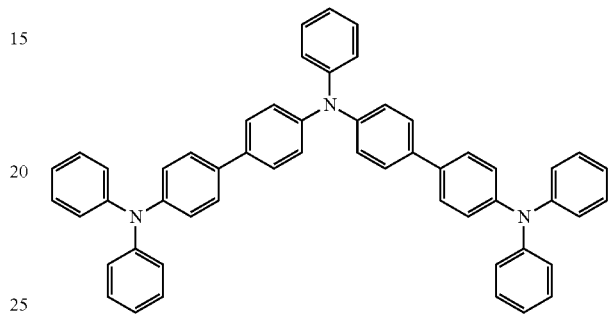

Example 8B

An organic EL device was prepared in the same manner as in Example 4B except that Compound 2-10 of the following structural formula was formed in a film thickness of 20 nm as the hole-injecting layer 3 in placed of Compound 2-1. The thus prepared organic EL device was measured for characteristics at ordinary temperature in the air.

The results of measuring the luminescence characteristics upon applying a direct current voltage to the prepared organic EL device are summarized and shown in Table 2.

[Compound 107]

(2-4)

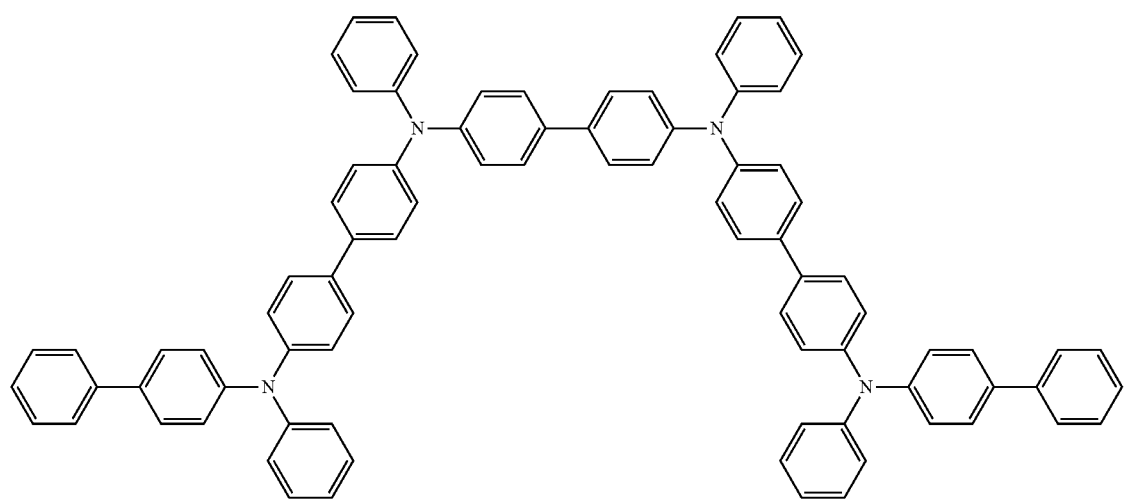

[Compound 109]

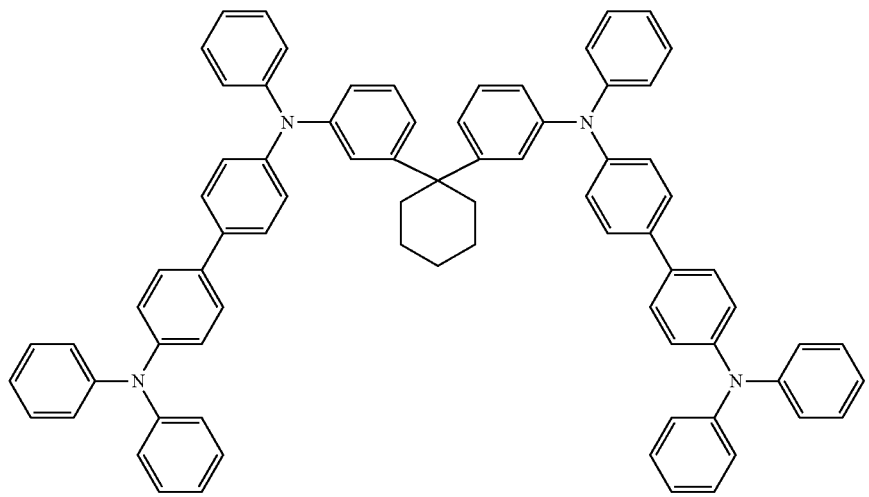

(2-10)

Example 9B

An organic EL device was prepared in the same manner as in Example 4B except that Compound 2-14 of the following structural formula was formed in a film thickness of 20 nm as the hole-injecting layer 3 in placed of Compound 2-1. The thus prepared organic EL device was measured for characteristics at ordinary temperature in the air.

The results of measuring the luminescence characteristics upon applying a direct current voltage to the prepared organic EL device are summarized and shown in Table 2.

[Compound 110]

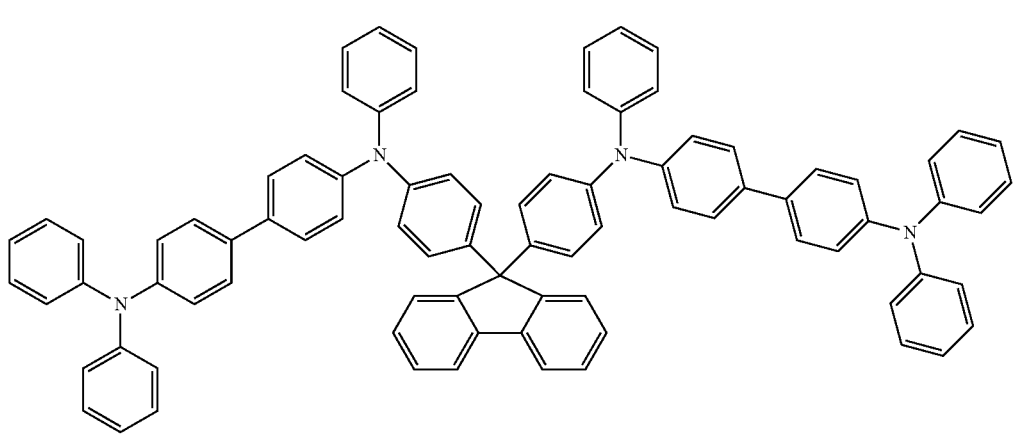

(2-14)

Example 10B

An organic EL device was prepared in the same manner as in Example 4B except that Compound 3-4 of the following structural formula was formed in a film thickness of 40 nm as the hole-transporting layer 4 in placed of Compound 3-1. The thus prepared organic EL device was measured for characteristics at ordinary temperature in the air.

The results of measuring the luminescence characteristics upon applying a direct current voltage to the prepared organic EL device are summarized and shown in Table 2.

[Compound 111]

(3-4)

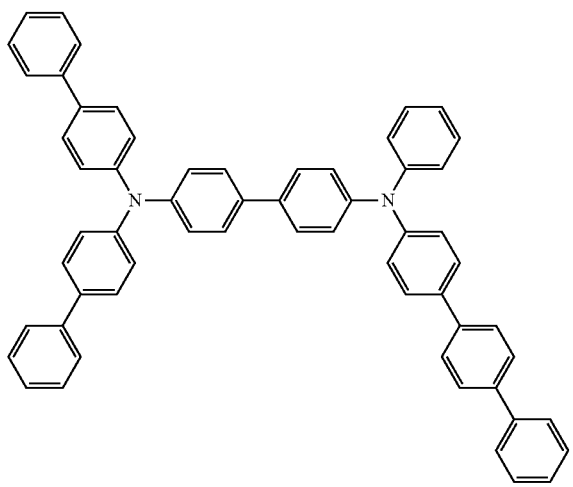

Example 11B

An organic EL device was prepared in the same manner as in Example 4B except that Compound 3-6 of the following structural formula was formed in a film thickness of 40 nm as the hole-transporting layer 4 in placed of Compound 3-1. The thus prepared organic EL device was measured for characteristics at ordinary temperature in the air.

The results of measuring the luminescence characteristics upon applying a direct current voltage to the prepared organic EL device are summarized and shown in Table 2.

[Compound 112]

(3-6)

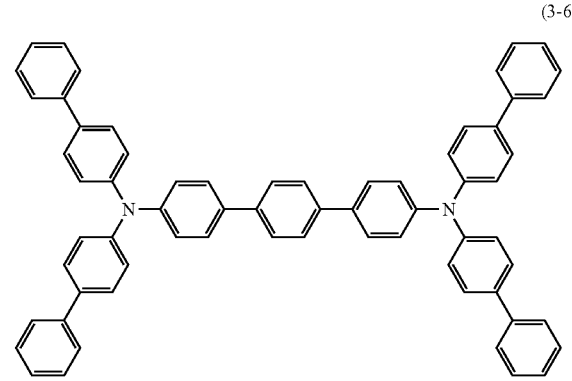

Example 12B

An organic EL device was prepared in the same manner as in Example 4B except that Compound 3-10 of the following structural formula was formed in a film thickness of 40 nm as the hole-transporting layer 4 in placed of Compound 3-1. The thus prepared organic EL device was measured for characteristics at ordinary temperature in the air.

The results of measuring the luminescence characteristics upon applying a direct current voltage to the prepared organic EL device are summarized and shown in Table 2.

[Compound 113]

(3-10)

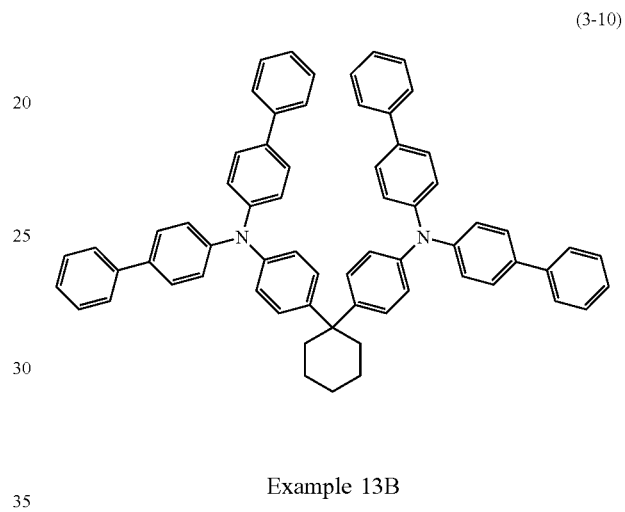

Example 13B

An organic EL device was prepared in the same manner as in Example 4B except that Compound 3-15 of the following structural formula was formed in a film thickness of 40 nm as the hole-transporting layer 4 in placed of Compound 3-1. The thus prepared organic EL device was measured for characteristics at ordinary temperature in the air.

The results of measuring the luminescence characteristics upon applying a direct current voltage to the prepared organic EL device are summarized and shown in Table 2.

[Compound 114]

(3-15)

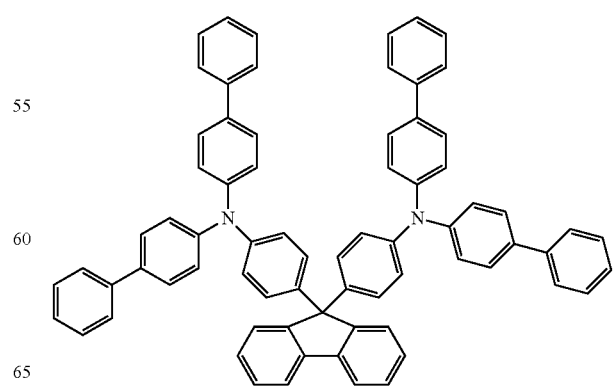

Referential Example 1B

An organic EL device was prepared in the same manner as in Example 2B except that Alq$_3$ was formed in a film thickness of 30 nm as the electron-transporting layer 7 in place of Compound 1-3. The thus prepared organic EL device was measured for characteristics at ordinary temperature in the air.

The results of measuring the luminescence characteristics upon applying a direct current voltage to the prepared organic EL device are summarized and shown in Table 1.

Comparative Example 1B

An organic EL device was prepared in the same manner as in Referential Example 1B except that CuPc was formed in a film thickness of 20 nm as the hole-injecting layer 3 in place of Compound 2-1. The thus prepared organic EL device was measured for characteristics at ordinary temperature in the air.

The results of measuring the luminescence characteristics upon applying a direct current voltage to the prepared organic EL device are summarized and shown in Table 1.

TABLE 1

|  | Voltage [V] (@10 mA/cm$^2$) | Current Efficiency [cd/m$^2$] (@10 mA/cm$^2$) | Power Efficiency [lm/W] (@10 mA/cm$^2$) |
| --- | --- | --- | --- |
| Example 2B | 4.58 | 11.15 | 7.65 |
| Example 3B | 4.08 | 12.24 | 9.44 |
| Example 4B | 3.85 | 12.66 | 10.34 |
| Example 5B | 4.76 | 11.35 | 7.50 |
| Referential Example 1B | 5.43 | 8.50 | 4.90 |
| Comparative Example 1B | 8.30 | 12.80 | 5.35 |

From Referential Example 1B and Comparative Example 1B, in the case of replacing the compound of the hole-injecting layer from CuPc to Compound 2-1, it was confirmed that the driving voltage is lowered but the current efficiency is lowered. It may be considered that this was caused due to the fact that because of an excessively high hole mobility of Compound 2-1, the hole carrier increased, and the carrier balance was upset, whereby the recombination establishment was lowered. Then, when the compound of the electron-transporting layer was replaced by the compound having a pyridine ring and a pyridoindole ring in its molecule (Compound 1-3, Compound 1-4, Compound 1-10 or Compound 1-20), which is a material having a high transporting rate of electron carrier, a lowering of the driving voltage and great enhancements of the current efficiency and power efficiency could be confirmed, as shown in Examples 2B to 5B. This demonstrates that the carrier balance between the hole carrier and the electron carrier was improved through a combination of a material with a high hole mobility and a material with a high transporting rate of electron carrier.

TABLE 2

|  | Voltage [V] (@10 mA/cm$^2$) | Current Efficiency [cd/m$^2$] (@10 mA/cm$^2$) | Power Efficiency [lm/W] (@10 mA/cm$^2$) |
| --- | --- | --- | --- |
| Example 6B | 3.92 | 12.51 | 10.50 |
| Example 7B | 4.13 | 11.36 | 8.67 |
| Example 8B | 4.06 | 12.49 | 9.69 |
| Example 9B | 4.02 | 12.60 | 9.86 |
| Example 10B | 3.87 | 12.62 | 10.27 |
| Example 11B | 4.01 | 12.07 | 9.45 |
| Example 12B | 3.94 | 12.50 | 9.99 |
| Example 13B | 3.90 | 12.53 | 10.13 |

It was found that the carrier balance of the inside of the organic EL device is improved through a combination of a specified arylamine compound and a specified pyridine derivative and that as compared with the conventional organic EL devices using CuPc or Alq$_3$, an organic EL device having high current efficiency and power efficiency, a low driving voltage and a long life can be realized.

While the invention has been described in detail and with reference to specific embodiments thereof, it will be apparent to one skilled in the art that various changes and modifications can be made therein without departing from the spirit and scope thereof.

The present application is based on Japanese Patent Application No. 2008-129340 filed on Mary 16, 2008 and Japanese Patent Application No. 2008-173023 filed on Jul. 2, 2008, and the contents are incorporated herein by reference.

INDUSTRIAL APPLICABILITY

In the organic EL device having a combination of specified two kinds of arylamine compounds and the organic EL having a combination of a specified arylamine compound and a specified pyridine derivative according to the invention, the luminous efficiency can be enhanced, the driving voltage can be lowered, and the durability of the organic EL device can be improved. For example, it has become possible to spread it onto applications of electric home appliances and illuminations.

DESCRIPTION OF REFERENCE NUMERALS AND SIGNS

1: Glass substrate
2: Transparent anode
3: Hole-injecting layer
4: Hole-transporting layer
5: Emitting layer
6: Hole-blocking layer
7: Electron-transporting layer
8: Electron-injecting layer
9: Cathode

The invention claimed is:

1. An arylamine compound represented by the following formula:

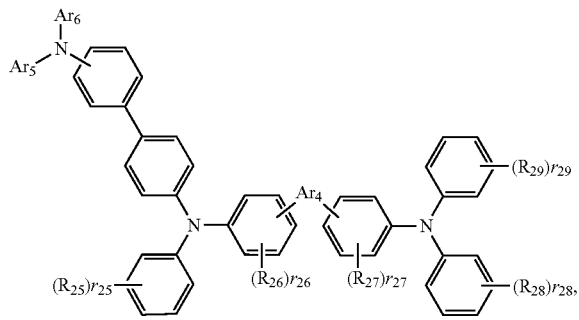

wherein:
$R_{25}$ independently represents a substituted or unsubstituted aromatic hydrocarbon group, or a substituted or unsubstituted condensed polycyclic aromatic group;
$R_{26}$ to $R_{29}$ independently represent a hydrogen atom, a substituted or unsubstituted aromatic hydrocarbon group, or a substituted or unsubstituted condensed polycyclic aromatic group;
when a plurality of the substituents $R_{25}$ to $R_{29}$ are bonded on the same benzene ring, they may be bonded to each other to form a ring;
$r_{25}$ to $r_{29}$ each represents an integer of from 1 to 4;
Ar4 represents a divalent group represented by the following structural formula (B):

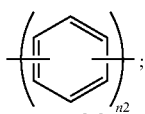
(B)

n2 represents an integer of from 1 to 3;
$Ar_5$ and $Ar_6$ independently represent a substituted or unsubstituted aromatic hydrocarbon group, with the proviso that at least one of $Ar_5$ and $Ar_6$ is represented by the formula:

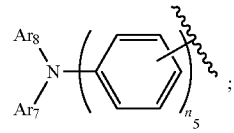

$Ar_7$ and $Ar_8$ independently represent a substituted or unsubstituted aromatic hydrocarbon group; and
$n_5$ represents an integer of from 2 to 3.

2. The arylamine compound according to claim 1, wherein n2 is 1.

3. The arylamine compound according to claim 1, wherein n2 is 2.

4. The arylamine compound according to claim 1, wherein $r_{25}$ to $r_{29}$ each is 1.

5. The arylamine compound according to claim 1, wherein the plurality of $R_{25}$ to $R_{29}$ is bonded on the same benzene ring and they are not bonded to each other to form a ring.

6. The arylamine compound according to claim 1, wherein at least one of $Ar_5$ and $Ar_6$ is a substituted aromatic hydrocarbon group.

7. The arylamine compound according to claim 1, wherein:
$Ar_5$ and $Ar_6$ both independently represent the formula:

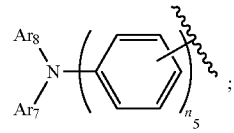

$Ar_7$ and $Ar_8$ independently represent a substituted or unsubstituted aromatic hydrocarbon group; and
$n_5$ represents an integer of from 2 to 3.

8. The arylamine compound according to claim 1, which is:

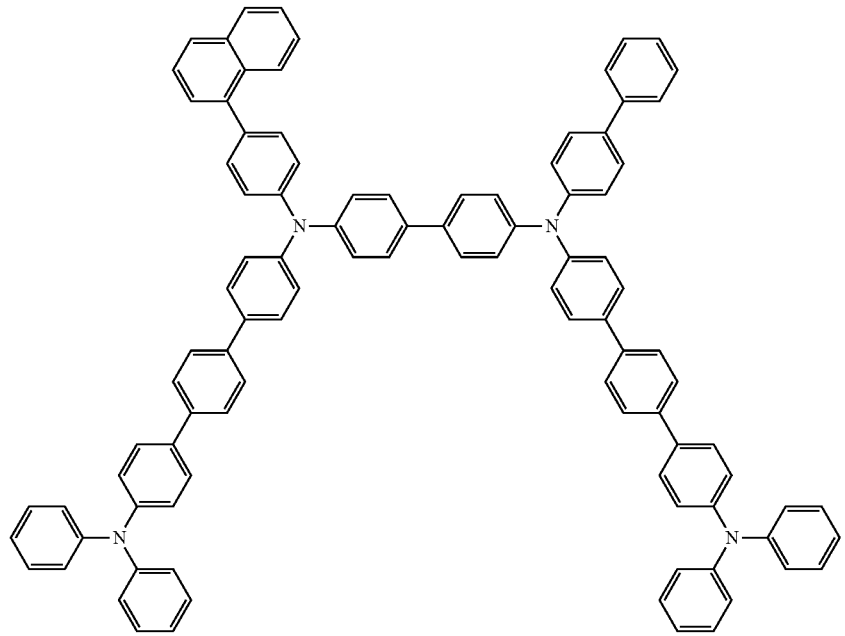

* * * * *